(12) United States Patent
Godavarty et al.

(10) Patent No.: US 11,464,453 B2
(45) Date of Patent: Oct. 11, 2022

(54) CELLPHONE BASED TISSUE OXYGENATION MEASURING DEVICE

(71) Applicants: Anuradha Godavarty, Miami, FL (US); Kacie Kaile, Miami, FL (US)

(72) Inventors: Anuradha Godavarty, Miami, FL (US); Kacie Kaile, Miami, FL (US)

(73) Assignee: THE FLORIDA INTERNATIONAL UNIVERSITY BOARD OF TRUSTEES, Miami, FL (US)

( * ) Notice: Subject to any disclaimer, the term of this patent is extended or adjusted under 35 U.S.C. 154(b) by 597 days.

(21) Appl. No.: 16/406,712

(22) Filed: May 8, 2019

(65) Prior Publication Data

US 2020/0352515 A1 Nov. 12, 2020

(51) Int. Cl.
*A61B 5/1455* (2006.01)
*A61B 5/00* (2006.01)
*A61B 5/145* (2006.01)
*A61B 5/1495* (2006.01)

(52) U.S. Cl.
CPC .......... *A61B 5/6898* (2013.01); *A61B 5/1495* (2013.01); *A61B 5/14546* (2013.01); *A61B 5/14552* (2013.01); *A61B 5/14556* (2013.01); *A61B 2560/0238* (2013.01)

(58) Field of Classification Search
CPC .............. A61B 5/1455; A61B 5/14551; A61B 5/14552; A61B 5/6898; A61B 5/14546; A61B 5/14556
See application file for complete search history.

(56) References Cited

U.S. PATENT DOCUMENTS

| 9,042,967 B2* | 5/2015 | Dacosta | A61B 5/72 |
| | | | 600/476 |
| 9,855,009 B2* | 1/2018 | Segman | A61B 5/14552 |
| 9,895,090 B2* | 2/2018 | Johnson | A61B 5/14552 |
| 10,905,331 B2* | 2/2021 | Vilenskii | A61B 5/1455 |
| 2014/0200054 A1* | 7/2014 | Fraden | H04M 1/7246 |
| | | | 455/575.8 |

OTHER PUBLICATIONS

Das, A. et al. "Mobile phone based mini-spectrometer for rapid screening of skin cancer," Jun. 2015, Proc, of SPIE vol. 9482, 5 pages.

(Continued)

*Primary Examiner* — Eric F Winakur
(74) *Attorney, Agent, or Firm* — Saliwanchik, Lloyd & Eisenschenk

(57) ABSTRACT

A cellphone-based oxygenation tool can include a circuitry housing unit, a light emitting diode (LED) box disposed on the circuitry housing unit, a plurality of LEDs disposed in the LED box, a diffuser sheet or lens disposed on the LED box, a lens holder disposed on the circuitry housing unit and configured to be movable with respect to the circuitry housing unit, a near-infrared (NIR) filter disposed on the lens holder, and a cellphone disposed on the circuitry housing unit and having an NIR sensitive camera. Each of the plurality of LEDs can have different wavelengths, and application software of the cellphone can be configured to acquire data from the NIR sensitive camera and process the data before storing the data.

18 Claims, 22 Drawing Sheets

(56) References Cited

OTHER PUBLICATIONS

Vanegas, M. et al. "Mobile Phone Camera Based Near-Infrared Spectroscopy Measurements," Biophotonics Congress: Biomedical Optics Congress 2018 Microscopy/Translational/Brain/OTS), OSA Technical Digest (Optical Society of America, 2018), paper JTu3A. 64, pp. 1-2.

Kaile, K. et al. "Development and Validation of a Smartphone-Based Near-Infrared Optical Imaging Device to Measure Physiological Changes In-Vivo," Micromachines, 2019, 10, 180, pp. 1-15.

\* cited by examiner

Generation A:

Generation B:

Generation C:

Generation D:

CELLPHONE BASED TISSUE OXYGENATION MEASURING DEVICE

BACKGROUND

Wound care management is rapidly expanding in treatment and preventive measures of diabetic foot ulcers (DFUs). The clinical standard of assessing healing is from visual assessment of wound color, degree of epithelization, and size reduction across weeks of treatment. Various biomarkers have been developed to complement visual wound assessment, which include histological detection and characterization of infection, and measurement of tissue oxygenation (TO) or vascularization. Oxygen supply to wounds is a vital factor for successful healing. Oxygenation and blood flow to wound site has been measured using Doppler ultrasound (DUS), transcutaneous oxygen measurements (TCOM), hyperspectral imaging (HSI), or near-infrared (NIR) spectroscopy (NIRS). These imaging tools are not readily available to clinicians and nurses in every hospital, private clinic, or during house visits in aged populations. Considering the prevalence of smartphones, assessing wounds by analyzing images of ulcers is an attractive alternative; if the device can provide subclinical physiological assessment of the wound (in terms of TO) in order to complement clinical visual wound assessment. Smartphone-based wound image analysis approach has been recently developed by researchers to capture high resolution digital images of the wound and determine the wound size via image segmentation algorithms.

DFU wound care management employs visual inspection of DFUs as a gold-standard approach to assess wound healing status. There are several challenges with current practices for treating DFUs. These include: (i) Visual clinical assessment of the wound by its color, degree of epithelization and size reduction across weeks of treatment—is a non-objective approach with no systematic or digitized tracking of healing status. (ii) The objective subclinical wound assessment tools such as histological detection (to characterize infection), Doppler ultrasound (to measure blood flow to wound required for healing), and transcutaneous oxygen measurement device (TCOM) or hyperspectral imaging, HSI (to measure extent of oxygenation to wound to aid healing)—provide physiological information, but are expensive, time consuming, and not available in all clinics as part of standard of care.

BRIEF SUMMARY

In view of the above, there is a need in the art for a low-cost, real-time, and objective wound assessment tool can become part of the standard of care for chronic ulcers, such as diabetic foot ulcers (DFUs). Embodiments of the invention include inexpensive mobile (e.g., smartphone-based) imaging tools that can digitally record and track wound healing status in real-time from subclinical physiological changes apart from clinical visual changes. Physiological changes manifest prior to visual reduction in wound size, allowing potential detection of serious complications early-on.

According to a 2015 HIMSS (Healthcare Information and Management Systems Society) Mobile Technology Survey, more than 200 healthcare provider employees found that nearly 90% of respondents are utilizing mobile devices within their organizations to engage patients in their healthcare. About 52% of smartphone users gather health-related information on their phones, and 80% of physicians use smartphones and medical apps. Thus, mobile (e.g., smartphone-based) technologies can be adapted by healthcare providers to objectively monitor wound healing status (pre- and post-operative) during routine wound care management. This has the potential to improve patient outcomes and transitional cases, without adding to total costs and time.

Recently, researchers have developed smartphone-based apps for 2D and 3D wound image analysis, track patients' wound healing status, and select appropriate wound dressings based on symptoms. Wound image analysis apps acquire digital images of the visual wound and apply algorithms to demarcate wound boundaries to estimate and track wound size reduction. These approaches do not provide any physiological assessment of the wound to augment clinical assessments that various expensive imaging tools (e.g., TCOM, Doppler ultrasound, HSI) provide. Hence, there is a need in the art to develop a low-cost add-on imaging tool to smartphones (SmartPhone Oxygenation Tool—SPOT) or cellphones (Cellphone-Based Oxygenation tool—CBOT), such that it records digital images of the wound (for size measurements) and physiologically assesses wound (from tissue oxygenation measurements). The terms SPOT and CBOT are used interchangeably herein. This is done even though it is recognized that not all cellphones are smartphones. Embodiments of the subject invention can be implemented using any cellphone, including but not limited to smartphones, even though the term SPOT may be used.

Physiological assessment of DFUs is vital to augment the clinician's assessment of a wound from sub-clinical information that is not visible to the naked eye. Oxygen supply to DFUs is a key limiting factor for successful healing due to increased demand for reparative processes such as cell proliferation, bacterial defense, angiogenesis and collagen synthesis. Prognostic imaging of tissue oxygenation (TO) is essential to assess the effectiveness of treatment approach in improving oxygen supply to wounds (and thus enhance healing rates). Hence, there is a need in the art to image for TO changes apart from recording visual changes to assess the healing status of DFUs, as proposed in this project.

Embodiments of the subject invention provide novel and advantageous mobile (e.g., cellphone-based or smartphone based) oxygenation tools that comprise a light source having multi-wavelength illumination, application software acquiring data and processing the data, and a cellphone with camera, thereby allowing a user to detect the amount of tissue oxygenation (and/or the hemoglobin concentration) contained in a region of interest and to store the data.

In an embodiment, a cellphone-based oxygenation tool can comprise: a circuitry housing unit; a light source case disposed on the circuitry housing unit; a lens holder disposed on the circuitry housing; and a light source disposed in the light source case.

In another embodiment, a cellphone-based oxygenation tool can comprise: a circuitry housing unit; a light source disposed on the circuitry housing unit and being configured to provide near-infrared (NIR) light; a lens holder disposed on the circuitry housing unit; and an NIR filter disposed on the lens holder. The light source can be, for example, a laser diode or a light emitting diode (LED) box having a plurality of LEDs disposed in the LED box. The NIR filter can be a long pass filter, bandpass filter, holographic filter, or combination thereof.

In yet another embodiment, a cellphone-based oxygenation tool can comprise: a circuitry housing unit; a light source disposed on the circuitry housing unit and being configured to provide NIR light; a diffuser sheet or diffuser lens disposed on the light source; a lens holder disposed on the circuitry housing unit and configured to be movable with respect to the circuitry housing unit; an NIR filter disposed on the lens holder; and a cellphone disposed on the circuitry housing unit and having a near-infrared (NIR) sensitive camera. The cellphone can comprise a processor and a (non-transitory) machine-readable medium (e.g., a (non-transitory) computer-readable medium) with instructions stored thereon that, when executed by the processor, acquire data from the NIR sensitive camera and process the data before storing the data. It is noted that the data can be stored before and/or after processing. The light source can be, for example, a laser diode or a light emitting diode (LED) box having a plurality of LEDs disposed in the LED box. If present, each LED of the plurality of LEDs can be a multi-wavelength LED configured to provide light at multiple different wavelengths. For example, four multi-wavelength LEDs can be present. The NIR filter can be a long pass filter, bandpass filter, holographic filter, or combination thereof.

In a further embodiment, fluorescence imaging can be performed using the CBOT, with appropriate choice of NIR filters, such that the illumination wavelength is eliminated and the fluorescence signal (at a higher wavelength) can be captured.

In yet another embodiment, a method of measuring tissue oxygenation using a cellphone-based oxygenation tool can comprise: emitting light through a light source connected to the cellphone; receiving an image through a filter fixed on the cellphone; processing an pixel intensity based on the image; converting the pixel intensity into oxygenated and deoxygenated hemoglobin concentrations; providing a tissue oxygenation map (or oxygen saturation) and/or a hemoglobin concentration map based on the oxygenated and deoxygenated hemoglobin concentrations; and storing the tissue oxygenation map and/or the hemoglobin concentration map (as oxy-hemoglobin, deoxy-hemoglobin, and/or total hemoglobin).

In yet another embodiment, the choice of light source wavelengths can be in the visible and/or near infrared spectrum(s) to image other tissue components including but not limited to water and melanin.

DETAILED DESCRIPTION

Figure 1A:
FIG. 1(a) shows a generation-A of technology using only cellphone applications.
Figure 1B:
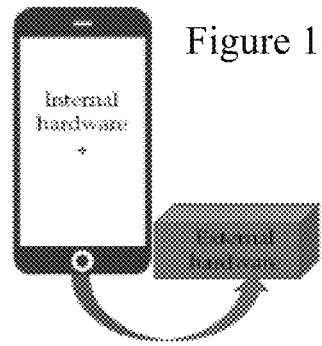
FIG. 1(b) shows a generation-B of technology using an external hardware with an internal hardware.
Figure 1C:
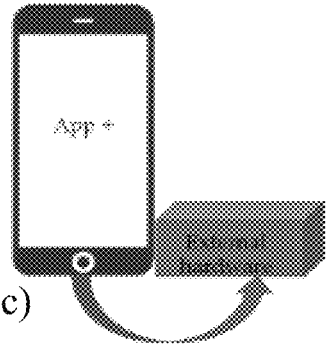
FIG. 1(c) shows a generation-C of technology using an application with an external hardware.
Figure 1D:
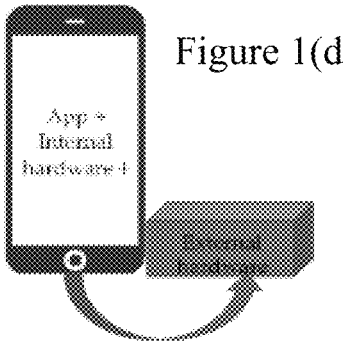
FIG. 1(d) shows a generation-D of technology combining internal and external hardware with cellphone-based applications.

Embodiments of the subject invention provide novel and advantageous mobile (e.g., cellphone-based or smartphone-based) oxygenation tools that comprise a light source having multi-wavelength illumination, application software acquiring data and processing the data, and a cellphone with camera, thereby allowing a user to detect the amount of tissue oxygenation (TO) and/or the hemoglobin concentration contained in a region of interest and to store the data.

In an embodiment, a hand-held near-infrared optical scanner (NIROS) that uses near-infrared (NIR) light (e.g., between 650-950 nm) is configured to (and used to) obtain spectroscopic (or physiological) information from beneath the tissue surface. As NIR light is minimally absorbed and preferentially scattered by tissues, it allows deep tissue imaging. NIROS can be used in multiple clinical sites to map TO changes in DFUs across days/weeks of treatment. Oxygenation maps acquired across days/weeks of treatment differentiate healing from non-healing wounds. Preliminary TO-based dynamic analysis demarcates regions of poor oxygen flow around DFUs. The oxygenation changes with healing and provides objective assessment to augment clinicians' visual assessment of wound healing, with a potential to dynamically alter treatment approach for improved standard of care. Based on NIROS, embodiments of the subject invention provide the smartphone-based Smart-Phone Oxygenation Tool (SPOT) NIR device or cellphone-based oxygenation tool (CBOT) as a low-cost, easy to use alternative to measure TO and/or hemoglobin concentration(s).

Smartphone based technology for health care can be categorized into four generations as shown in FIG. 1. Generation-A (Gen-A) technology utilizes only the smartphone and its built-in internal hardware and application software (or app). Examples of Gen-A technology include measuring heart rate and tissue oxygen saturation. Gen-B technology utilizes external hardware (or devices) attached to the smartphone along with its internal hardware, but there is no associated processing or application software (or apps). An example of a Gen-B device is the Forward Looking Infrared Radiometer (FLIR) device, which is an attachable external component that allows the user to measure heat. The device utilizes both internal and external hardware with no additional processing features, resulting in real-time data detection. Gen-C technology utilizes information from external devices to be considered as input to an installed app; that is, internal hardware of the phone is not utilized. An example of Gen-C technology is an attachable pulse oximeter (external hardware) connected to the smartphone, for the purpose of utilizing its app and providing a visual output. Gen-D technology involves the integration of external hardware (or device) with the smartphone's internal hardware, along with custom-developed apps for data processing and display. Examples of Gen-D technology include attachable spectrometers that can determine spectra when attached to the smartphone's camera.

CBOT is a smartphone-based NIR spectrometer for non-contact area imaging developed using Gen-D based smartphone technology. To date, NIR spectroscopic imaging has been developed into smartphone attached spectrometers for various applications (e.g., brain imaging, skin cancer). However, these devices acquire discrete point-based physiological information of tissues via contact imaging (not appropriate for wound imaging). CBOT is the only area based spectrometer that can obtain physiological (TO and/or hemoglobin concentration) information of large tissues (e.g., wounds) without contact.

CBOT is a smartphone-based device to physiologically assess wounds. Smartphone-based wound image analysis approach has been recently developed by researchers to: (a) capture 2D digital images of wound and determine its size via image segmentation algorithms; (b) determine the wound depth in 3D; (c) select appropriate wound dressing based on symptoms; and/or (d) track wound healing status of patients. Considering the prevalence of smartphones, these smartphone-based approaches to digitize wound images and determine depth is important to make clinical assessments objective. Assessing wounds from a subclinical physiological perspective is a novel addition to smartphone-based technologies that augments wound care management with a potential to predict serious complications early on. To date, there is no smartphone-based imaging technology that physiologically assesses the wound bed (as TO and/or hemoglobin concentration-based measurements). CBOT devices according to embodiments of the subject invention are innovatively developed to obtain non-contact, non-invasive TO measurements in wound care management.

CBOT is a low cost add-on imaging tool with user-friendly app. The CBOT device is a low-cost add-on imaging tool to any smartphone (e.g., Android platform, Apple platform, other cellphone platforms) with a custom-app that synchronizes data acquisition, analysis, storage, and secured Wi-Fi transfer to electronic medical record systems (if required). The device is designed to be compatible with at least 4 generations of Android-based smartphones, allowing its plug-n-use from multiple phones. Integration of CBOT device's data to hospital electronic clinical records and its ease of use by staff will allow sustainability of the technology. Other advantages include the ability to use a secured cloud account or remote server (e.g., FTP server) for the data and the ability to download the data directly from the cellphone (e.g., using USB or other data transfer methods).

Technology associated with embodiments of the subject invention emerges from the last (fourth) generation and includes an external device+a mobile detector+a software application for the purpose of assessing tissue oxygenation. With this combination, embodiments of the subject invention provide a device capable of detecting subcutaneous TO changes that has a wide variety of applications. The device is intended to be a form of unofficial self-testing. Devices of a similar type have proven useful in saving lives when a user noticed irregularities in heartbeat or breathing patterns. Observing changes in TO may serve as an equally useful biomarker, especially for many patients who require daily treatment plans. The device, used in combination with the cellphone app, allows the user to detect the amount of TO (and/or the hemoglobin concentration) contained in a region of interest and stores the data to be compared over time. Additional dynamic assessment features can be added to enhance the capabilities to obtain real-time hemodynamic changes of the imaged regions.

Some main features of embodiments the subject invention include: (i) a simple clip-on or add-on light source that allows multi-wavelength illumination of tissues for static as well as dynamic imaging; (ii) application software that performs both data acquisition as well as data processing to obtain tissue oxygenation maps (both static and dynamic images); (iii) the ability of the add-on tool to adapt to any smartphone with camera features; and (iv) the ability to provide dynamic and/or perfusion maps apart from tissue oxygenation maps (or any hemoglobin concentration-based parameter maps, or even simple diffuse reflectance, absorption, or fluorescence maps) of tissues imaged.

Figure 2:
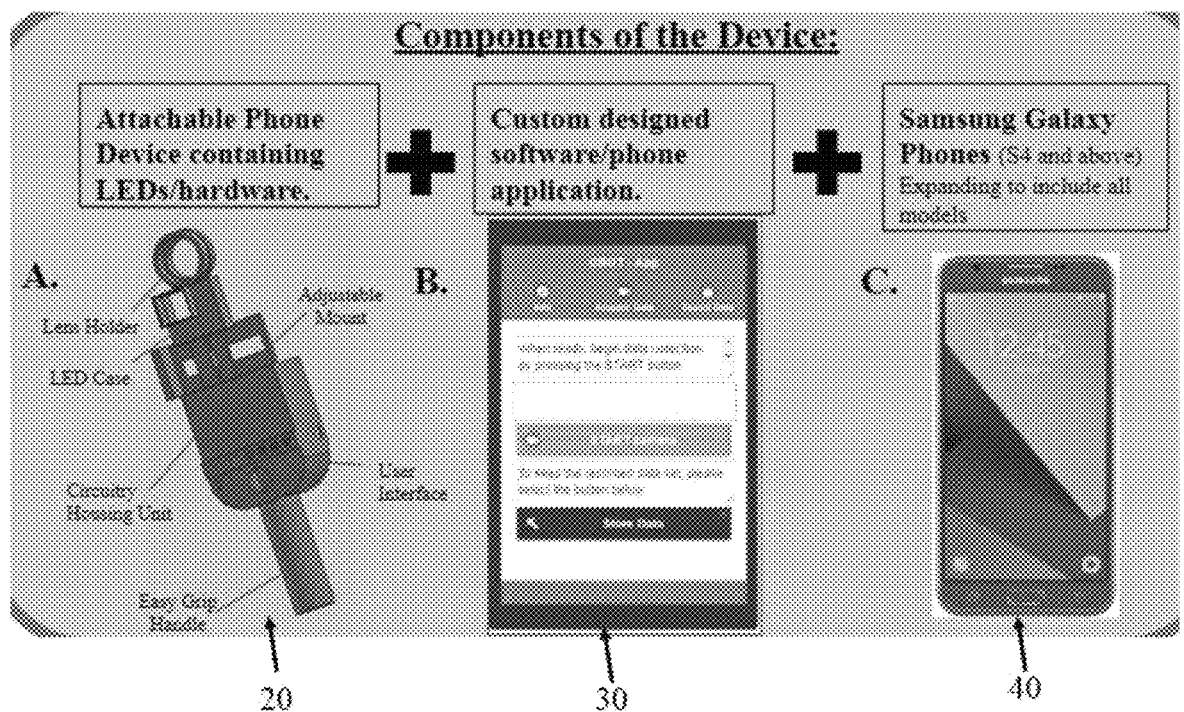
FIG. 2 shows overview of a device and the necessary components of a cellphone-based oxygenation tool according to an embodiment of the subject invention.

FIG. 2 shows overview of a device and the necessary components of a cellphone-based oxygenation tool according to an embodiment of the subject invention. Referring to FIG. 2, a cellphone-based oxygenation tool 10 comprises a cellphone add-on tool 20 as an attachable mount, cellphone application software 30, and a user's cellphone 40. The diagnostic tool is LED based, assessing a target area for changes in tissue oxygenation. Data is acquired using the cellphone's internal hardware as a detector, in combination with the attached device (external hardware). The cellphone-based oxygenation tool 10 is an attachable phone device containing LEDs/hardware 20, and the application software 30 is a custom designed software/phone application.

Collected information is processed internally by the cellphone application or externally (e.g., using a laptop or desktop computer). The device provides the user with the ability to compare tissue oxygenation in and around a region of interest. Data can be collected and compared through time to determine if oxygenation to the affected area is changing. Oxygenation trends can be a predictor in terms of tissue viability and with the ability to self-monitor can better treat patients experiencing less than normal tissue function. In addition to the potential to self-monitor, it is also possible for a technician, clinician, or other health care professional to monitor.

FIGS. 3(a)-3(e) show details of a cellphone add-on tool of a cellphone-based oxygenation tool according to an embodiment of the subject invention. Referring to FIGS. 3(a)-3(e), the cellphone add-on tool 20 comprises at least one printed circuit board (PCB) (not shown) and a 3D printed circuitry housing unit 100 that supports an NIR filter 142 (e.g., a long pass filter, bandpass filter, holographic filter, or a combination thereof) and offers a supportive base. For example, two PCBs (not shown) can be included. A polarizer lens or sheet can optionally be included, though this is not necessary.

The cellphone add-on tool 20 of the cellphone-based oxygenation tool comprises the circuitry housing unit 100, a light emitting diode (LED) box (or light source case) 122 disposed on the circuitry housing unit 100, a lens holder 140 disposed on the circuitry housing unit 100, and at least one NIR filter 142 (e.g., a long pass filter, bandpass filter, holographic filter, or a combination thereof) disposed on the lens holder 140.

The circuitry housing unit 100 comprises a first housing 110 corresponding to a cellphone and a second housing 120 including the LED box 122. The first housing 110 is used for a first PCB of the two PCBs and includes a start button 112, an ON button 114 controlling the on/off operation, and an indicator light 116 corresponding to each wavelength of a light source. In addition, a handle 160 (e.g., a removable handle) can be attached to the first housing 110 for easy grip handle.

The second housing 120 is used for a second PCB of the two PCBs and includes the LED box 122 for a light source. The LED box 122 includes a diffuser sheet (or lens) slot 124, and a diffuser sheet is disposed in the diffuser sheet (or lens) slot 124 of the LED box 122. The diffuser sheet (or lens) 126 can be a diffuser lens or sheet, and/or a polarizer lens or sheet.

The lens holder 140 is disposed on the second housing 120, and the longpass filter 142 is disposed on the lens holder 140. For example, the longpass filter 142 is a 645 nm filter, wherein NIR passes through the longpass filter 142 and UV and visible is blocked by the longpass filter 142 based on the 645 nm wavelength.

The cellphone add-on tool 20 further comprises an adjustable mount 130 disposed between the first housing 110 and the second housing 120. The adjustable mount 130 comprises a horizontal adjuster 132 allowing horizontal adjustment and a vertical adjuster 134 allowing vertical adjustment (such that it can be adjusted to any smartphone and respective camera location), thereby allowing the lens holder 140 and the second housing 120 to move with respect to the first housing 110.

Figure 3A:
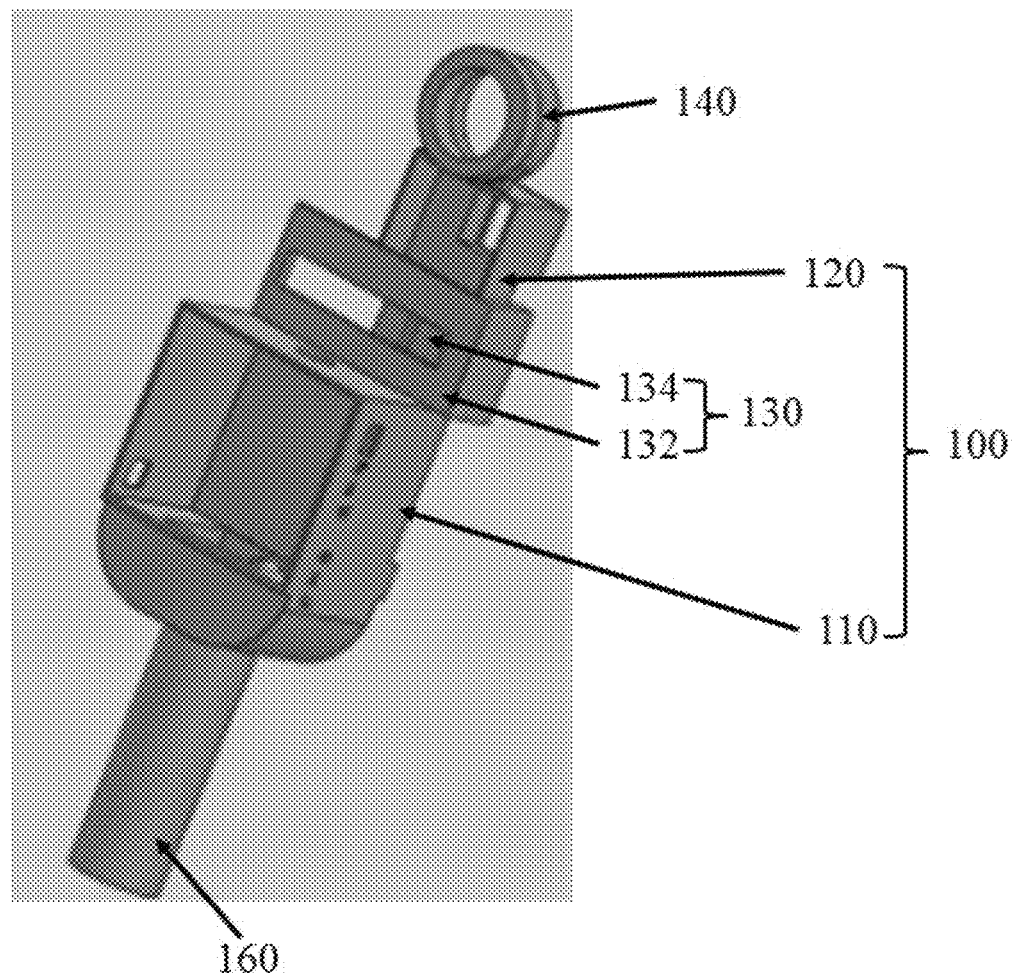
FIG. 3(a) shows a perspective view of a cellphone add-on tool of a cellphone-based oxygenation tool according to an embodiment of the subject invention.
Figure 3B:
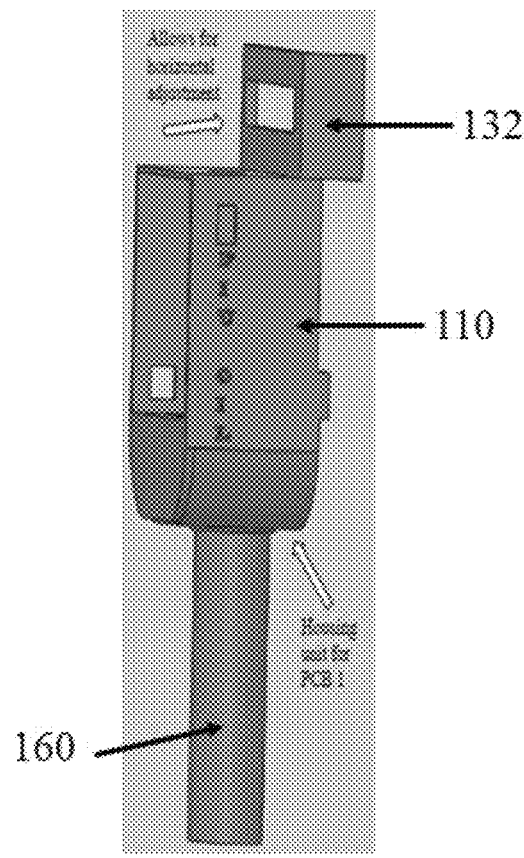
FIG. 3(b) shows a lower part of a cellphone add-on tool of a cellphone-based oxygenation tool according to an embodiment of the subject invention.
Figure 3C:
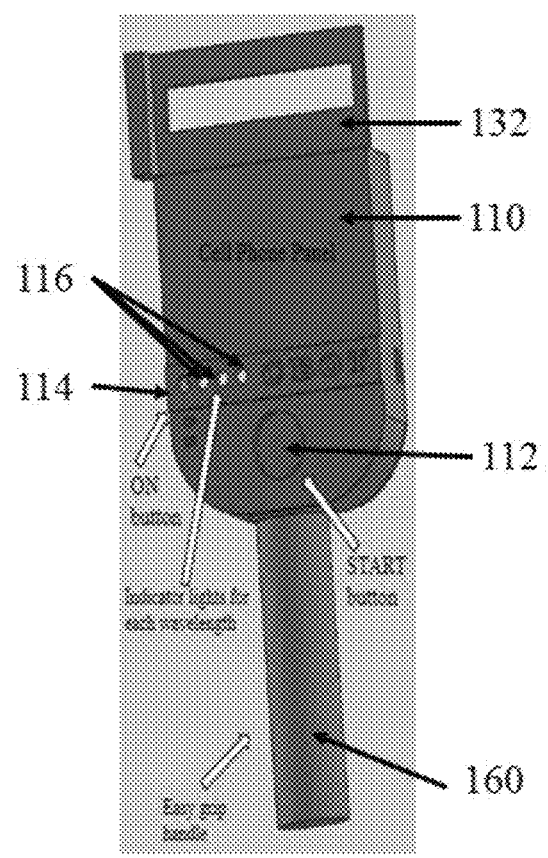
FIG. 3(c) shows another view of a lower part of a cellphone add-on tool of a cellphone-based oxygenation tool according to an embodiment of the subject invention.
Figure 3D:
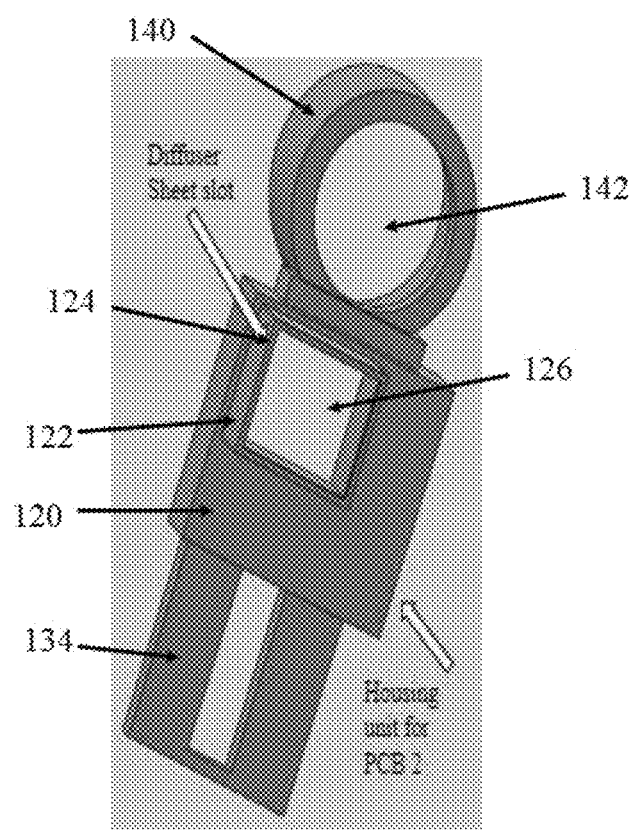
FIG. 3(d) shows an upper part of a cellphone add-on tool of a cellphone-based oxygenation tool according to an embodiment of the subject invention.
Figure 3E:
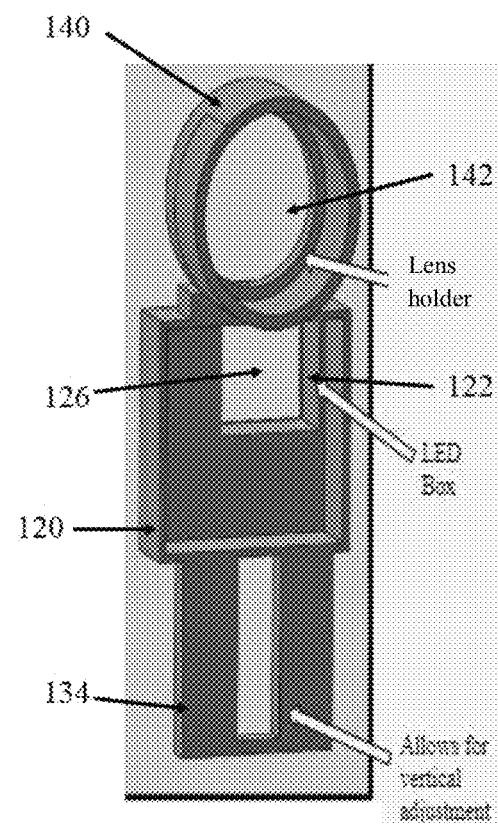
FIG. 3(e) shows an upper part of a cellphone add-on tool of a cellphone-based oxygenation tool according to an embodiment of the subject invention.
Figure 4:
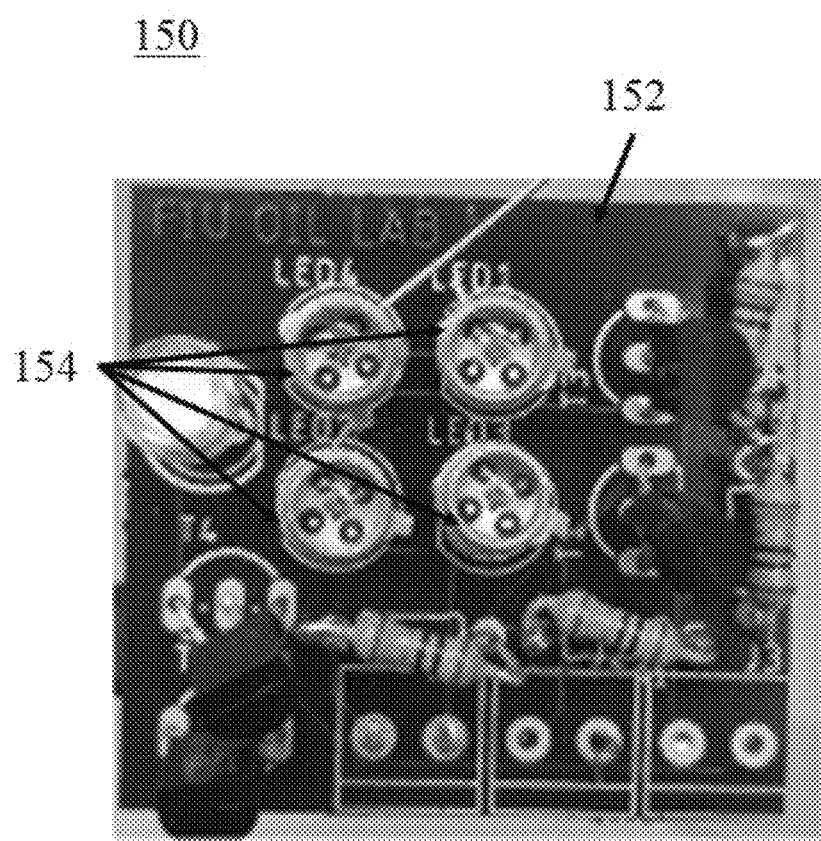
FIG. 4 shows a light emitting diode board of a cellphone-based oxygenation tool according to an embodiment of the subject invention.

FIG. 4 shows a light emitting diode board, a light emitting diode, and a light emitting diode circuitry of a cellphone-based oxygenation tool according to an embodiment of the subject invention, respectively. Referring to FIGS. 3(a)-4, the cellphone add-on tool 20 further comprises a light source 150 disposed in the light source case (or LED box) 122. The light source 150 comprises a LED board 152 and a plurality of LEDs 154 disposed on the LED board 152. Each LED of the plurality of LEDs 154 can be a multi-wavelength LED configured to provide light at multiple different wavelengths. For example, each LED can provide light at a wavelength of 690 nm, 750 nm, 800 nm, and/or 850 nm. That is, each LED can provide light at all specified wavelengths in a multi-wavelength LED, each LED can provide light at a single wavelength, or any combination of LEDs can be used (e.g., where some provide light at all specified wavelengths in a multi-wavelength LED and some provide light at a single wavelength).

The device operates with multi wavelength LED's in a common anode orientation, powered by power source (e.g., a battery, such as a 3.7 V rechargeable lithium ion battery). The light source 150 is placed to correspond to the diffuser sheet 126 (or diffuser lens) and/or polarizer lens or polarizer sheet), apart from a reflective surface for the LED box 122 to maximize the output optical power of the light source.

Figure 5:
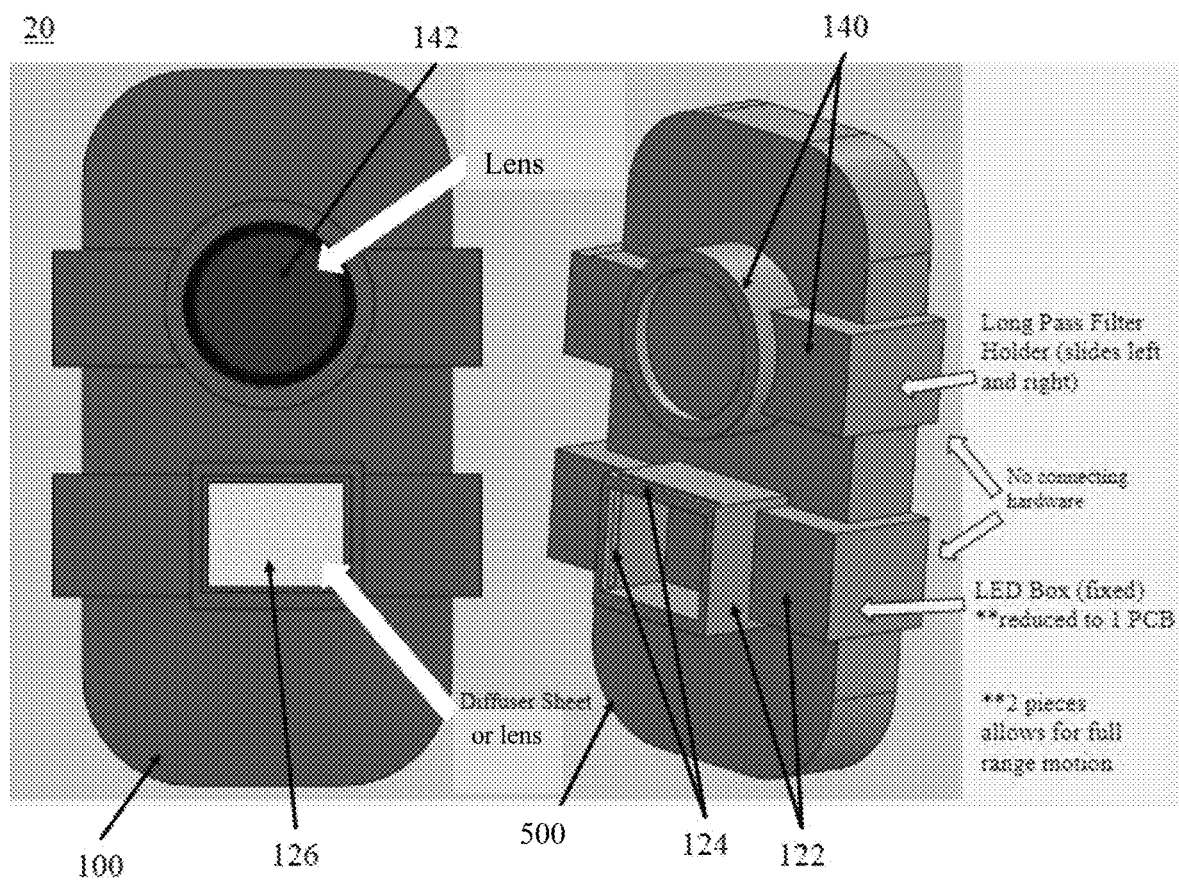
FIG. 5 shows a cellphone add-on tool of a cellphone-based oxygenation tool according to an embodiment of the subject invention.
Figure 6A:
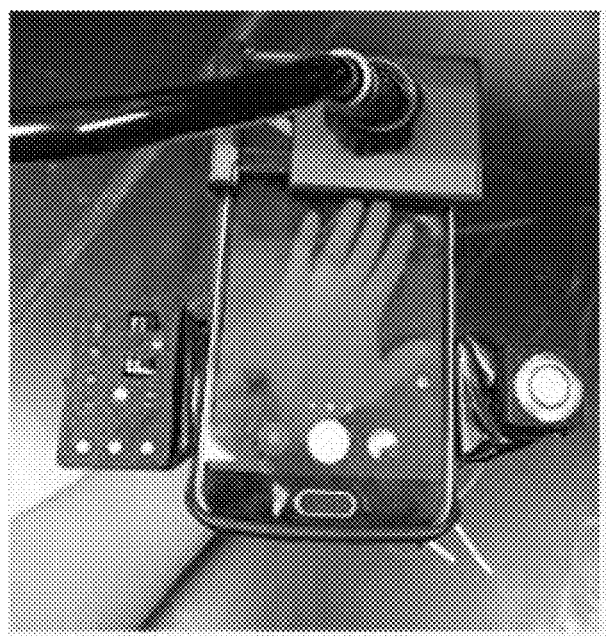
FIG. 6(a) shows a cellphone-based oxygenation tool according to an embodiment of the subject invention.
Figure 6B:
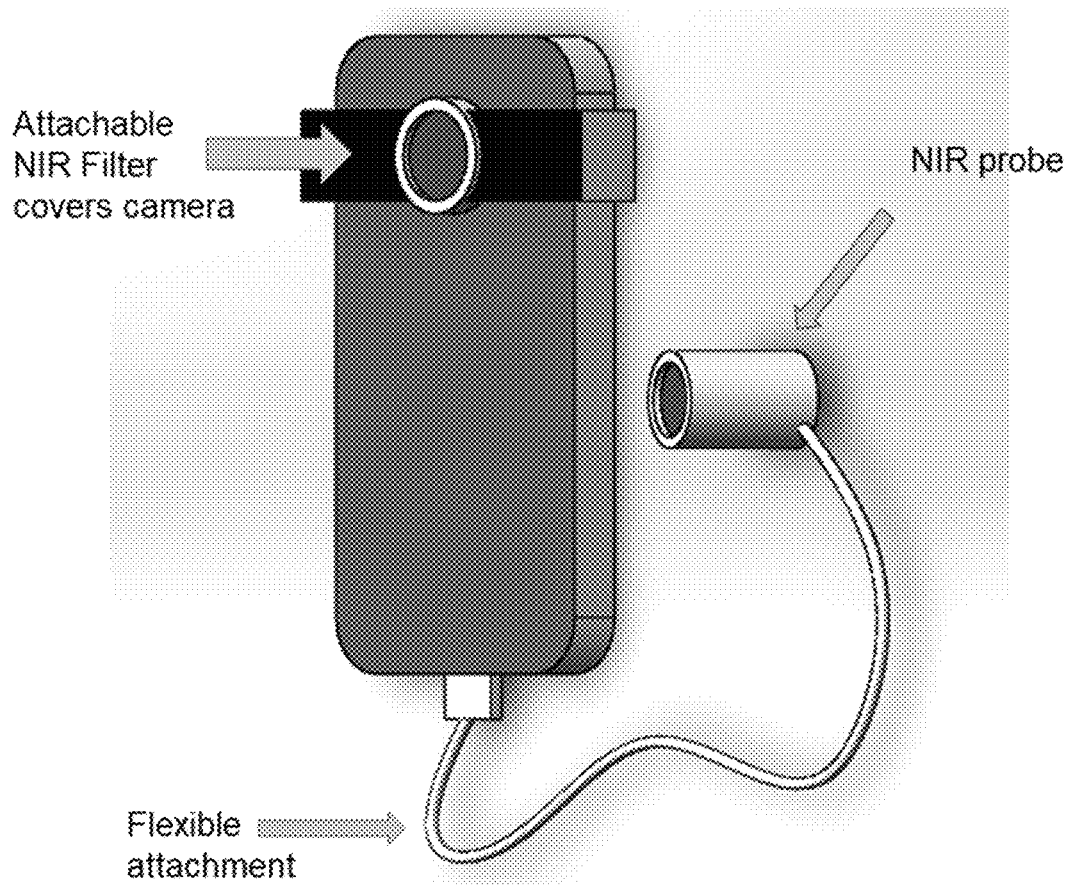
FIG. 6(b) shows a cellphone-based oxygenation tool with a flexible handle for illumination according to an embodiment of the subject invention.

FIGS. 5 and 6 show CBOTs according to embodiments of the subject invention. FIG. 5 shows a cellphone add-on tool of a CBOT according to an embodiment of the subject invention. Referring to FIG. 5, the cellphone 500 does not include a separated first housing 110 and second housing 120. Thus, the LED box 122 and the lens holder 140 are disposed on the cellphone 500, which can be thought of as a one piece circuitry housing unit 100 (the cellphone 500 houses circuitry therein). However, while the LED box 122 can be fixed (e.g., clipped) on the cellphone 500, the lens holder 140 is configured to slide left and right with respect to the cellphone 500. The LED box 122 can also slide left and right with respect to the cellphone 500.

Referring to FIG. 6(*a*), the device shows an attachable device without a hand mount, and user interface indicates LED function and output wavelength. In this embodiment, more user information is required in selecting wavelengths or mode of operation. Instead of controlling the LEDs and their multiplexing by the cellphone (e.g., via an app), switches and/or indicator lights are present. FIG. 6(*b*) shows another embodiment incorporating a moving source probe such that the device is capable of reflectance, transmittance (or transmission), and/or adjacent imaging flexibly from any angle/position with respect to the region being imaged. In all of these designs, the device can be made smaller by possibly incorporating surface mount technology (SMT) for the LED's and assisting circuitry or similar technologies that are more concise to package the light sources (LED's or other wavelength-specified sources). The LED of embodiments of the subject invention can be controlled by the App, for example using a Bluetooth switch.

Figure 7:
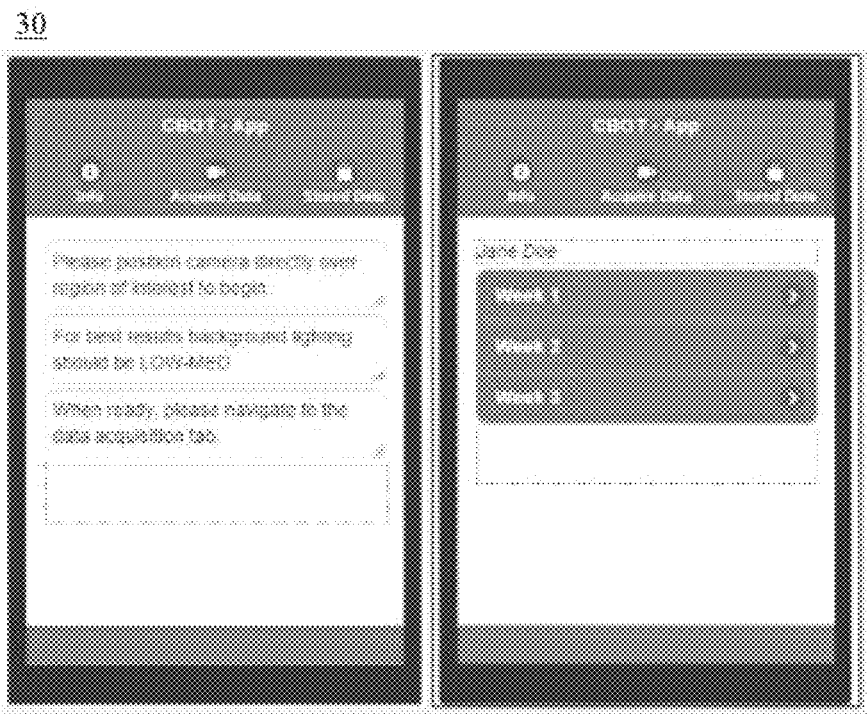
FIG. 7 shows an application of a cellphone-based oxygenation tool according to an embodiment of the subject invention.

FIG. 7 shows an application of a cellphone-based oxygenation tool according to an embodiment of the subject invention. Referring to FIG. 7, the application software 30 is the cellphone-based oxygenation tool (CBOT) phone application that works as an intermediate in data acquisition and storage. For example, video data can be streamed into Matlab for processing, using the IP camera add on. Video streamed data can be processed and stored in the app for future use. The software is being developed so that the app not only acquires the data and stores raw data, but also processes it before storing the processed data. With this addition, the cellphone-based tissue oxygenation app can have many features for different applications. The data acquisition and processing will involve open source software such as Python, C-Sharp, Java, and/or other higher programming languages and not commercially available Matlab or similar software.

The application software 30 operates a cellphone camera and the LED driver and also synchronizes them during data acquisition, saves external data obtained by the cellphone camera, streams/receives images into/from external data processing software (e.g., Matlab), and stores timestamped data. In addition, the application software 30 can operate video recorder, process images entirely within the App, and perform data analysis to acquire diffuse reflectance, absorption, and/or hemoglobin concentration maps (in terms of oxy-hemoglobin, deoxy-hemoglobin, total hemoglobin, oxygen saturation, and other relevant tissue physiological parameters such as melanin and water). This analysis can be for a single time stamp image (i.e., static) or for a continuous stream of time stamp (i.e., dynamic) images. The application software 30 is also able to record and track weekly or periodically acquired data from the same subject or across subjects.

Figure 8:
FIG. 8 shows a cellphone of a cellphone-based oxygenation tool according to an embodiment of the subject invention.

FIG. 8 shows a cellphone of a cellphone-based oxygenation tool according to an embodiment of the subject invention. Referring to FIG. 8, the cellphone 40 is the added cellphone held by the user. The device has been designed to accommodate many different cellular devices. The only requirement for the system is that the cellphone is NIR-sensitive (or has its NIR blocking filter removed from its camera). Currently, the add-on attachment in FIG. 8 is compatible to android based phones as their camera is NIR sensitive, but embodiments are not limited thereto.

As the background ambient lighting of the cellphone 40 can interfere, the medium indoor lighting can be used. The cellphone 40 can include video recorder using 60 fps option (or other speeds available in the cellphone). In addition, the cellphone 40 can be configured for the application software to control all modes (single wavelength or multi-wavelength imaging) before opening the video recorder, and use raw detected NIR images.

Figure 9:
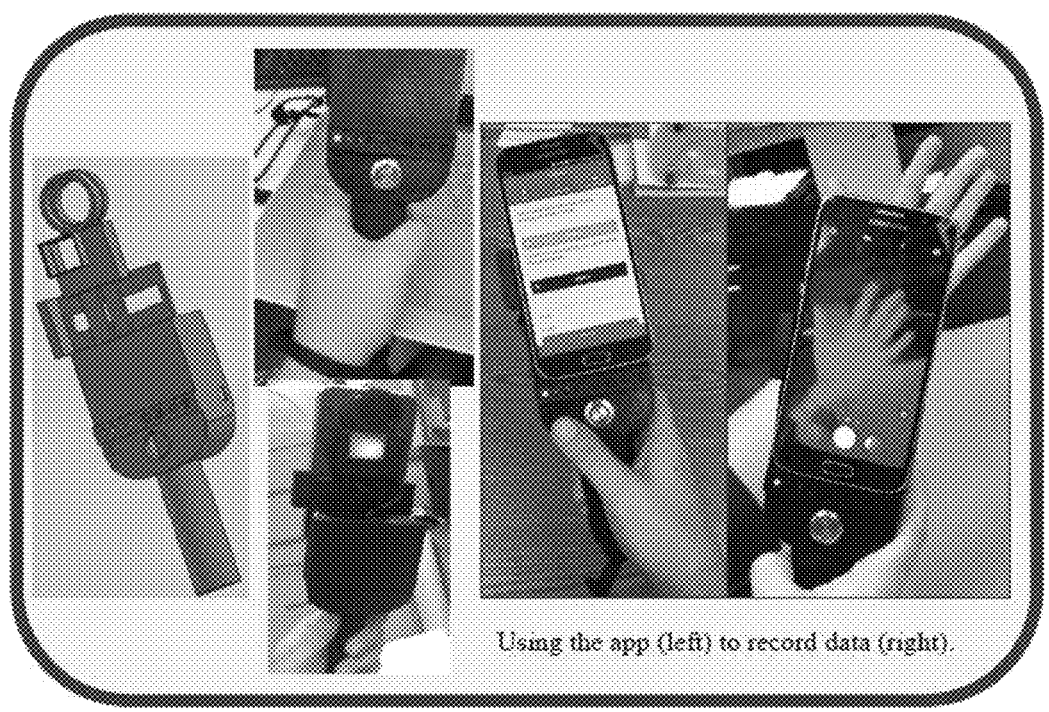
FIG. 9 shows images of a cellphone-based oxygenation tool according to an embodiment of the subject invention.

FIG. 9 shows images of a CBOT according to an embodiment of the subject invention. Referring to FIG. 9, with all components including the cellphone add-on tool 20, the application software 30, and the cellphone 40 together, the device functions as a tissue oxygenation tool that can quickly assess a region of interest for oxygen content, compared to its surroundings. Additional features of the device may provide for a dynamic assessment of tissue (e.g., for perfusion changes), and comparison of these maps over time (e.g., across milliseconds, seconds, minutes, or days) may be useful for monitoring chronic conditions.

Figure 10:
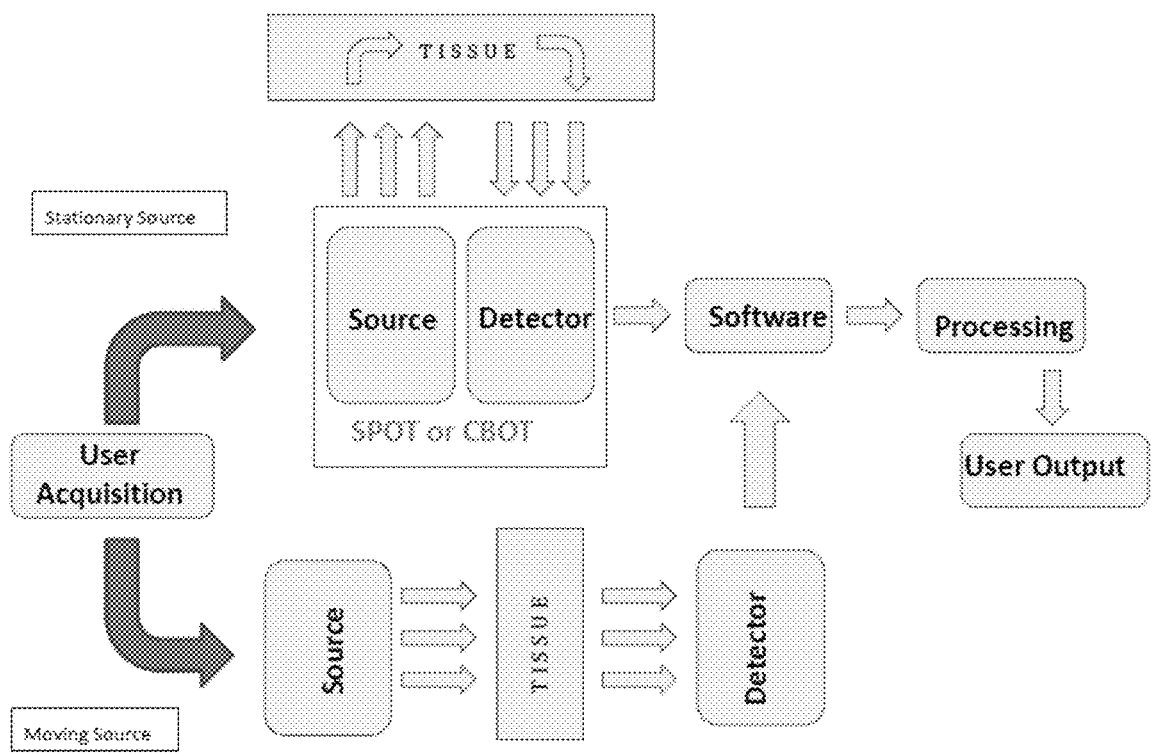
FIG. 10 shows a system overview of a cellphone-based oxygenation tool according to an embodiment of the subject invention.

The hardware portion of the device can be an attachable unit that can be secured to any cellphone for the purpose of supplying light signals (in multiple wavelengths), using the cellphone for detection. FIG. 10 shows a system overview of a cellphone-based oxygenation tool according to an embodiment of the subject invention. Referring to FIG. 10, the user fixes the cellphone on the attachable unit and then turns on the device. The light source (e.g., laser dioses (SMT or through hole), LEDs, or broad spectrum light source) connected to the cellphone faces the tissue and the detector (including NIR filter) detects the status of the tissue. The source can be a moving source using a flexible attachment disposed between the cellphone and the SMT LED probe or a stationary source in which the LED is fixed on the cellphone. The detected status of the tissue is processed via the software and then outputted for user.

Figure 11A:
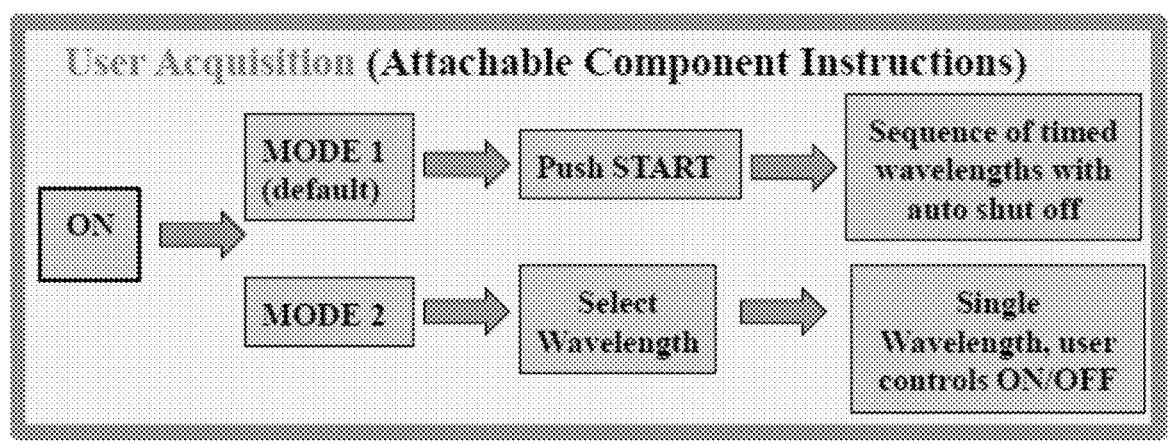
FIG. 11(a) shows modes of a cellphone-based oxygenation tool according to an embodiment of the subject invention.
Figure 11B:
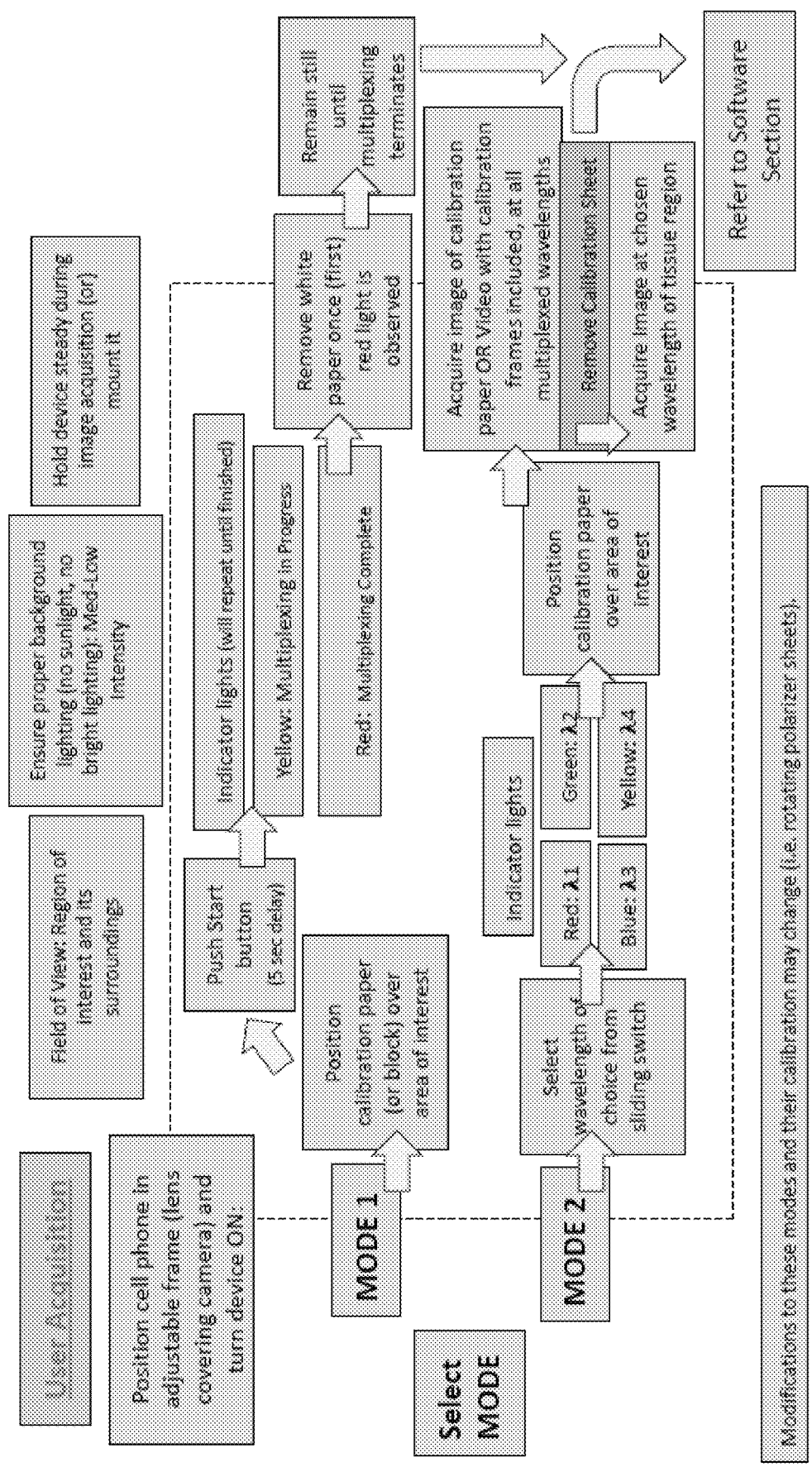
FIG. 11(b) shows a user acquisition of a cellphone-based oxygenation tool according to an embodiment of the subject invention.
Figure 12A:
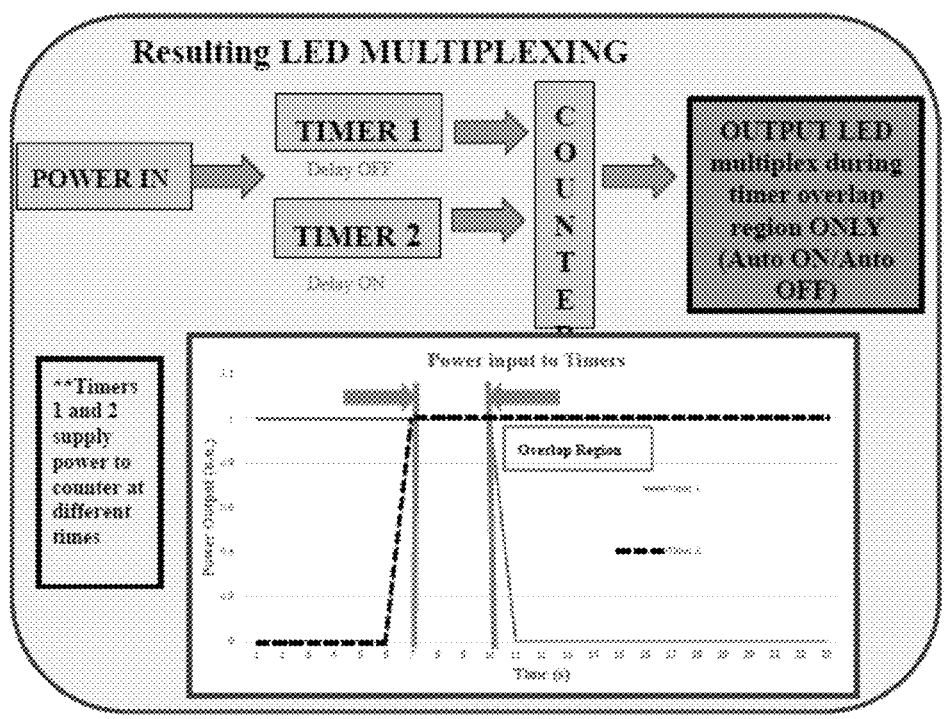
FIG. 12(a) shows a multiplexing sequence scheme of a light source of a cellphone-based oxygenation tool according to an embodiment of the subject invention.

FIG. 11(*a*) shows an abridged version of user acquisition of a CBOT according to an embodiment of the subject invention. Referring to FIGS. 12(*a*) and 12(*b*), the device operates on two modes, but the default (MODE 1) is designed to work by a single push button. The device multiplexes across multiple wavelengths of the light source that align with absorption spectra for HbO, HbR, and/or HbT (total hemoglobin) chromophores (and any other relevant chromophores in the wavelength spectra employed here, i.e. 600-1000 nm). FIG. 11(*b*) shows an expanded version of user acquisition of a CBOT according to an embodiment of the subject invention. Referring to FIGS. 10, 11(*a*), and 11(*b*), the user holds the device steady during image acquisition, confirms that the field of view contains the entire region and the surrounding region, and ensures the proper background lighting. In addition, the user can select to do either single-wavelength or multi-wavelength imaging.

FIG. 12(*a*) shows a multiplexing sequence scheme of a light source of a cellphone-based oxygenation tool according to an embodiment of the subject invention. Referring to FIG. 12(*a*), the source light multiplexing sequence is given at a 5 second delay from initiation (pressed start button) of device to allow for stability of the system and to select start of data retrieval within the application (where the cellphone's camera currently controls the starting point of data collection). Alternatively, the application software can be used to control the external switch (or start button) that controls light source and synchronize illumination and detection (by the cellphone's camera).

The resulting light multiplexing will continue for 4 seconds in which 2 cycles will revolve. At the end of the light multiplexing, the user can either terminate the video file in the application by pushing the stop button, or allow the application to terminate the video file after a predetermined time interval (less than 10 seconds).

Figure 12B:
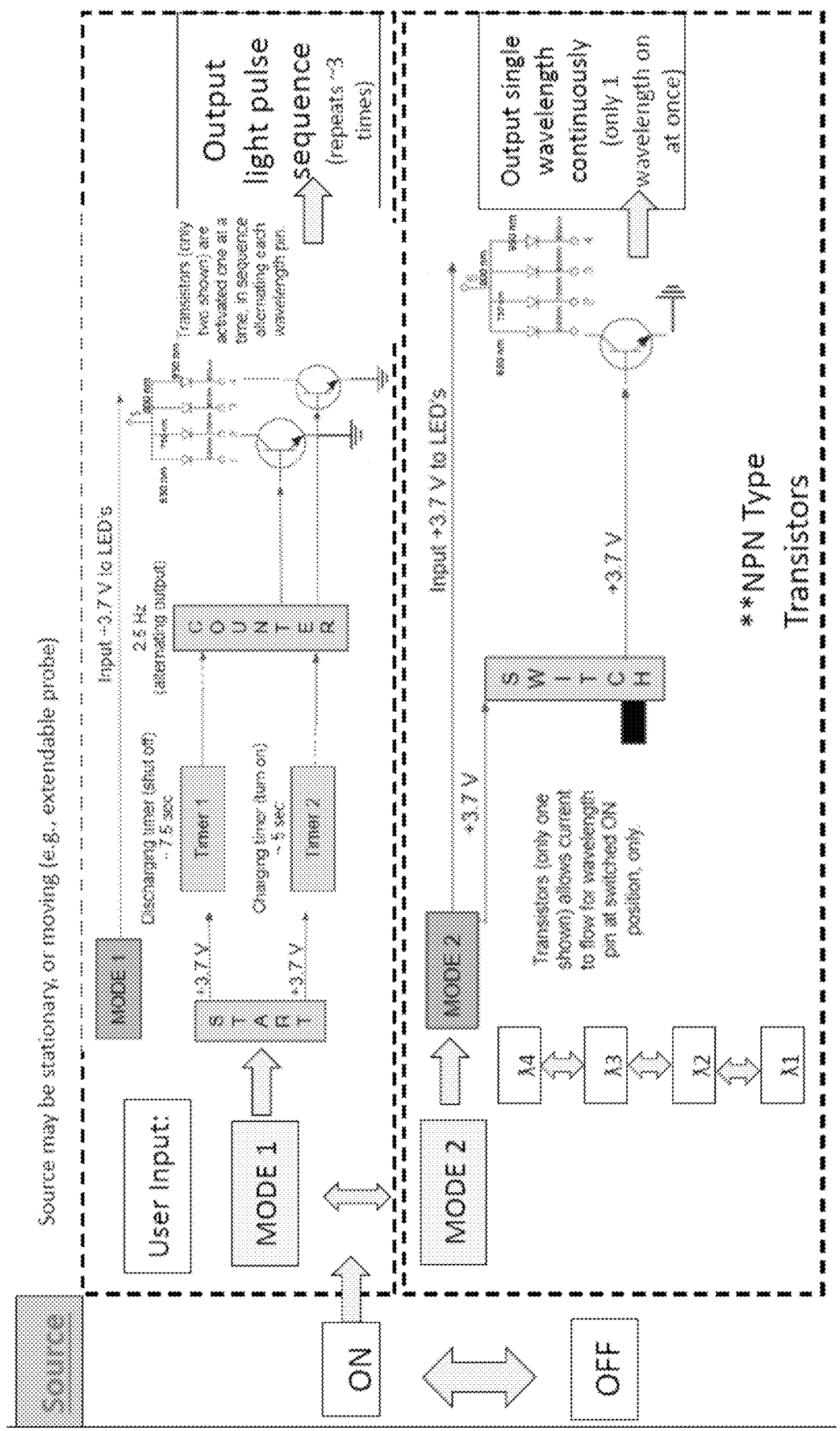
FIG. 12(b) shows detailed modes of a light source of a cellphone-based oxygenation tool according to an embodiment of the subject invention.
Figure 12C:
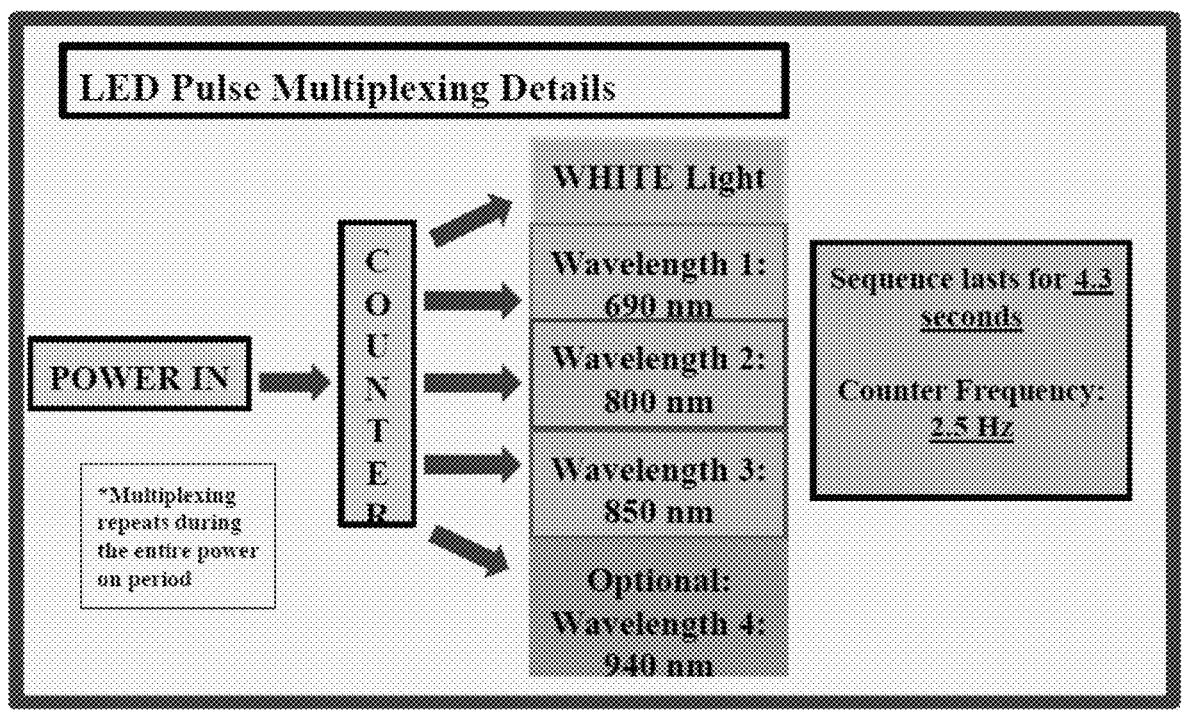
FIG. 12(c) shows a detailed pulse sequence scheme of a light source of a cellphone-based oxygenation tool according to an embodiment of the subject invention.

FIG. 12(b) shows modes of a CBOT according to an embodiment of the subject invention. FIG. 12(c) shows a detailed multiplexing scheme of a light source of a CBOT according to an embodiment of the subject invention. Referring FIG. 12(c), multiple wavelength (here, four) LEDs output between 600-1000 nm light across an area of tissue to be considered. In addition, white light can emit before and after 3 (or more) successive wavelengths between 600-1000 nm light.

Figure 13A:
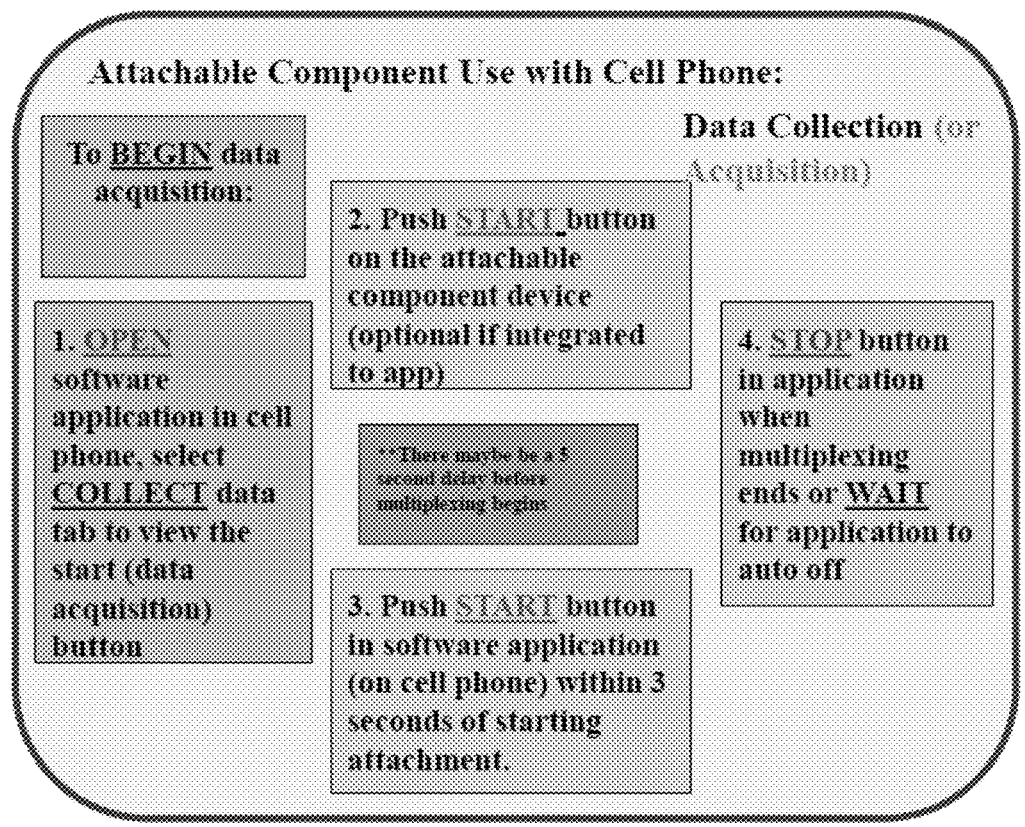
FIG. 13(a) shows a descriptive map to acquire data of a cellphone-based oxygenation tool according to an embodiment of the subject invention.

The cellphone is attached to measure the diffuse reflected signal at each wavelength. The circuitry allows for the LED sequence to be pulsed only for a short period of time (about 2 cycles), after delaying for 5 seconds. FIG. 13(a) shows a descriptive map to acquire data of a cellphone-based oxygenation tool according to an embodiment of the subject invention.

Figure 13B:
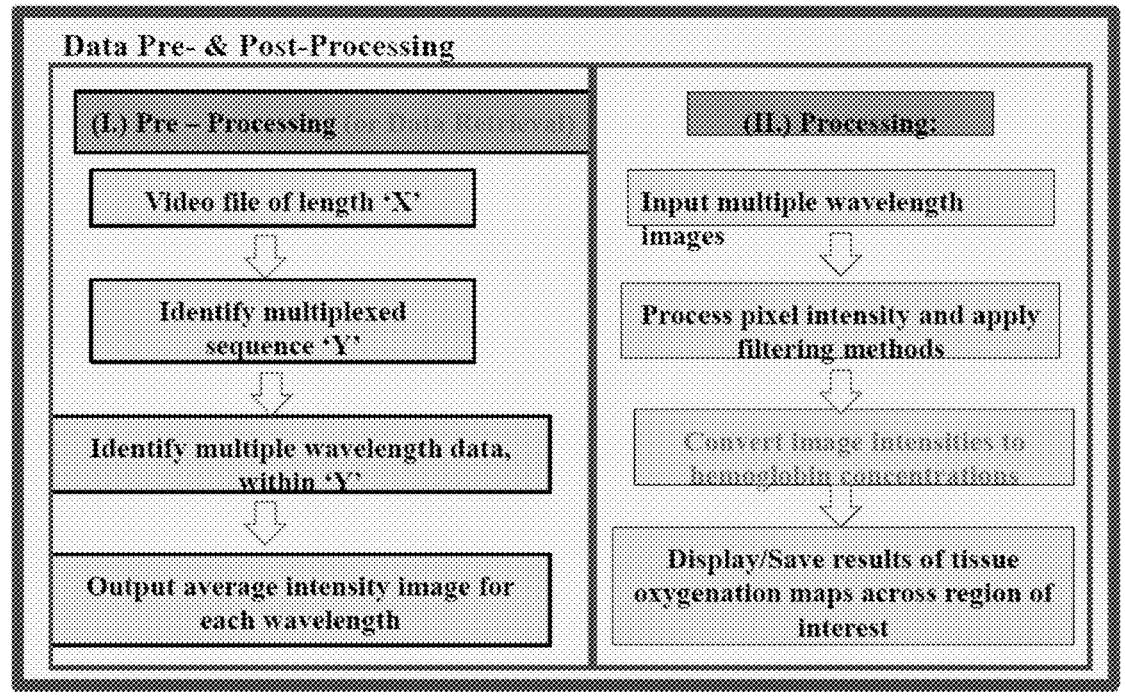
FIG. 13(b) shows processing steps from a raw image to output representation of data of a cellphone-based oxygenation tool according to an embodiment of the subject invention.
Figure 13C:
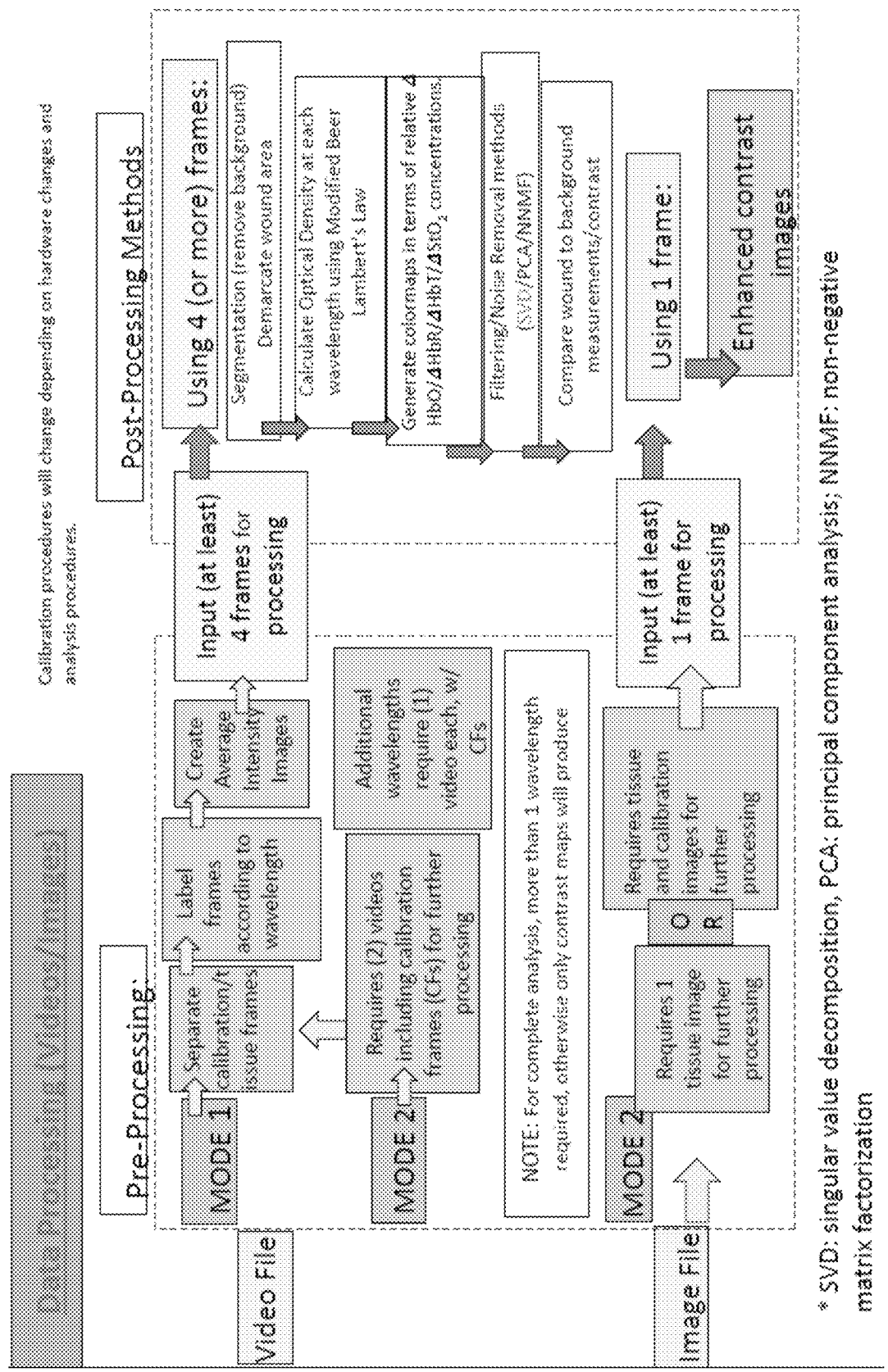
FIG. 13(c) shows detailed processing steps of a cellphone-based oxygenation tool according to an embodiment of the subject invention.

FIG. 13(b) shows an overview of data acquisition and processing steps from a raw image to output representation of data of a cellphone-based oxygenation tool according to an embodiment of the subject invention. If the data set is acquired without excessive movements, or outside light artifacts, the data will be selected for processing and analysis. Once this selection has been made, the application will go through the following data sequence. The data collected for further processing by the application is a video file of length 'x'. The file is first processed by obtaining the interval length of the multiplexed (multi-wavelength light) sequence. The length of each video file does not need to be the same because the white light pulse indicates the beginning and ending of a single cycle of multiplexed (multi-wavelength) light sources. Each multiplexed (multi-wavelength light) sequence is in equivalent time intervals. Within the multiplexed (multi-wavelength light) sequence, three (or any number that are activated in the hardware) wavelengths can be discretized. Frame rate of acquisition by the cellphone camera and the multiplexing frequency can be changed to sync illumination and detection. FIG. 13(c) shows detailed processing steps of a CBOT according to an embodiment of the subject invention.

Figure 14A:
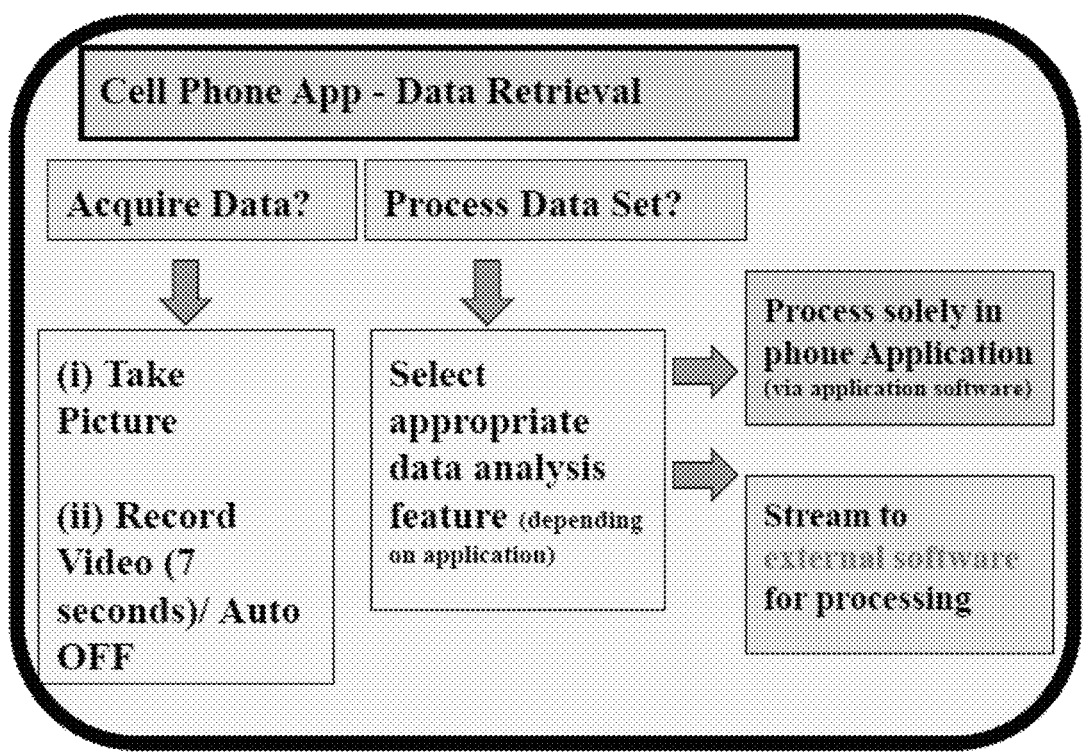
FIG. 14(a) shows a flowchart for data retrieval in an application of a cellphone-based oxygenation tool according to an embodiment of the subject invention.
Figure 14B:
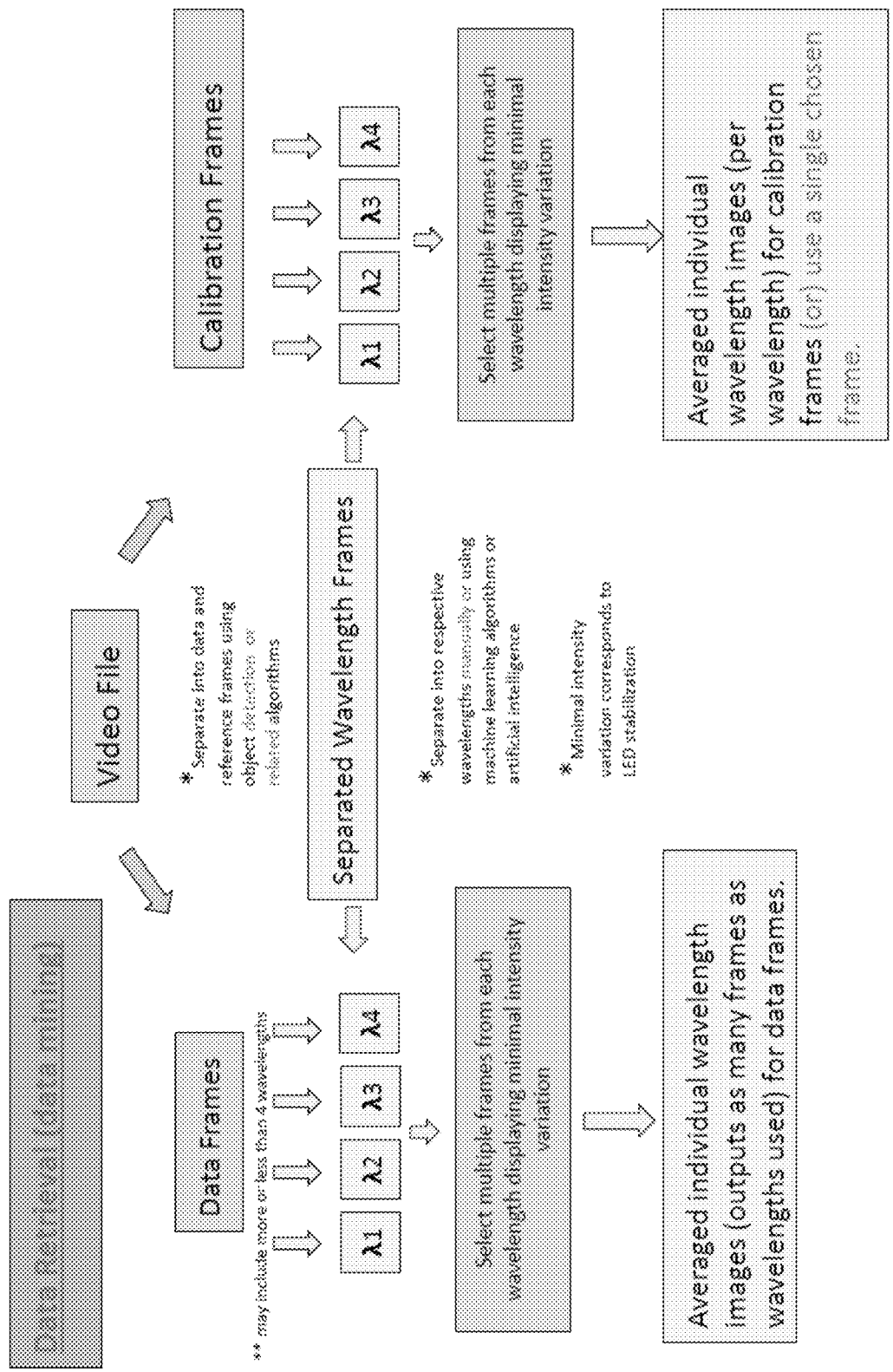
FIG. 14(b) shows data mining of the processing steps of a cellphone-based oxygenation tool according to an embodiment of the subject invention.

FIG. 14(a) shows a flowchart (or options) for data retrieval in an application of a cellphone-based oxygenation tool according to an embodiment of the subject invention. The application software has been developed to work in combination with the attachable device. In the event that no pulse sequence is witnessed coming from the attached device, the resulting video file will be discarded. The cellphone-based "app" (i.e., application software) will allow the user to select when ready to begin data acquisition as shown in FIG. 14(a). Also, the user selects if they want to acquire images in picture mode or video mode. Picture mode is used when imaging using a single wavelength illumination. Video mode is used when multi-wavelength data is acquired continuously for a single cycle across all the chosen wavelengths at a given time point or across a period of time (for dynamic imaging studies). FIG. 14(b) shows data mining of the processing steps of a CBOT according to an embodiment of the subject invention.

Figure 15:
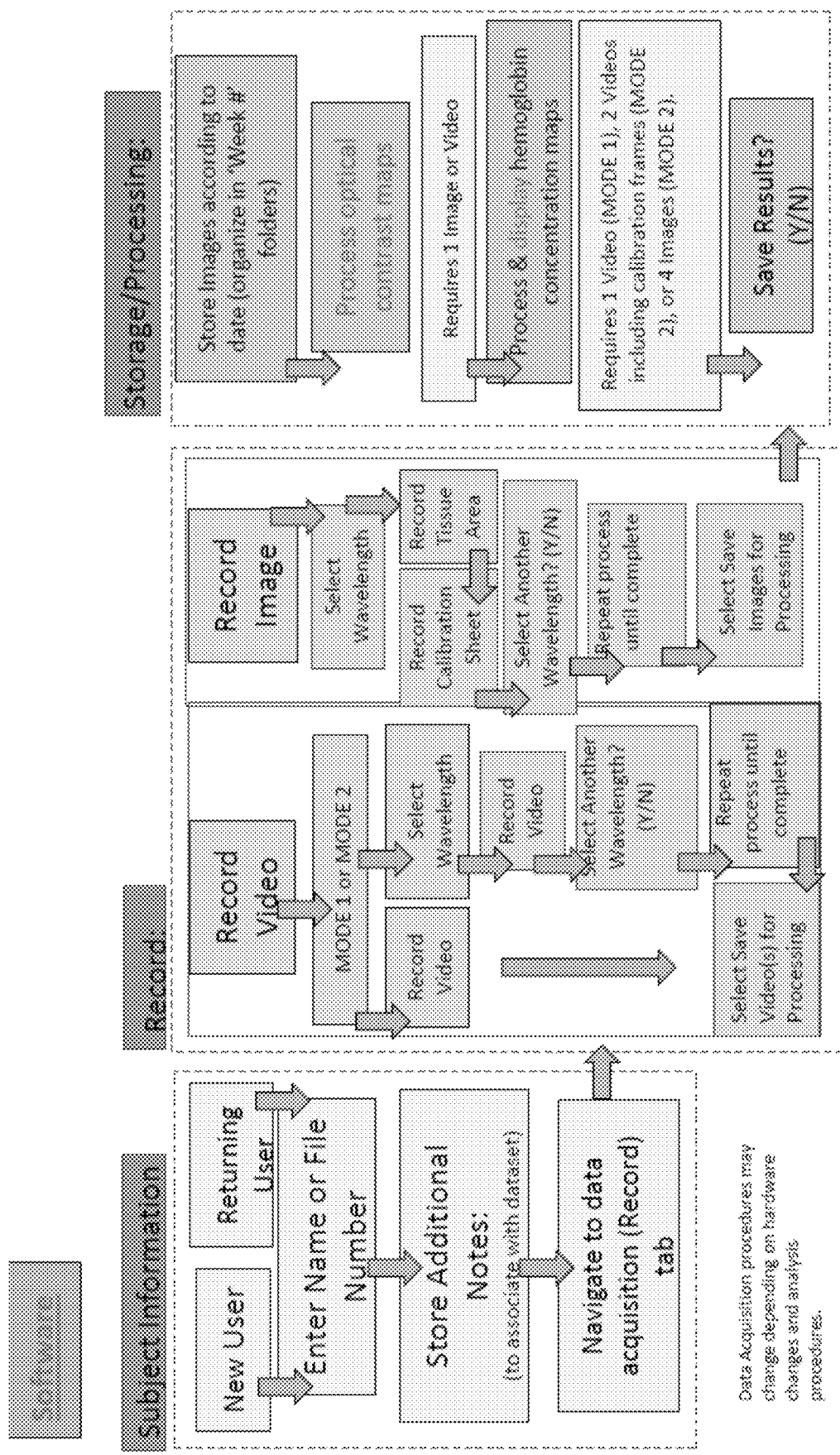
FIG. 15 shows a software operation of a cellphone-based oxygenation tool according to an embodiment of the subject invention.

FIG. 15 shows a software operation (or application software) of a cellphone-based oxygenation tool according to an embodiment of the subject invention. Referring to FIG. 13(a), the overall instructions for hardware data acquisition can be shown in four steps. In another embodiment, a microcontroller (or similar control devices) may be programmed (firmware programming) to allow different variations in the sequence and repetitions of specific wavelengths of each LED of the multiple LEDs to illuminate as a chosen pattern. This is just one such method to operate the light sources. Referring to FIG. 15, the software can acquire data and control the recording of a video or an image. In addition, the software can process optical contrast maps, hemoglobin concentration maps (i.e. HbO, HbR, HbT, $StO_2$) and/or other tissue chromophores such as water and melanin, and then save the results.

Figure 16A:
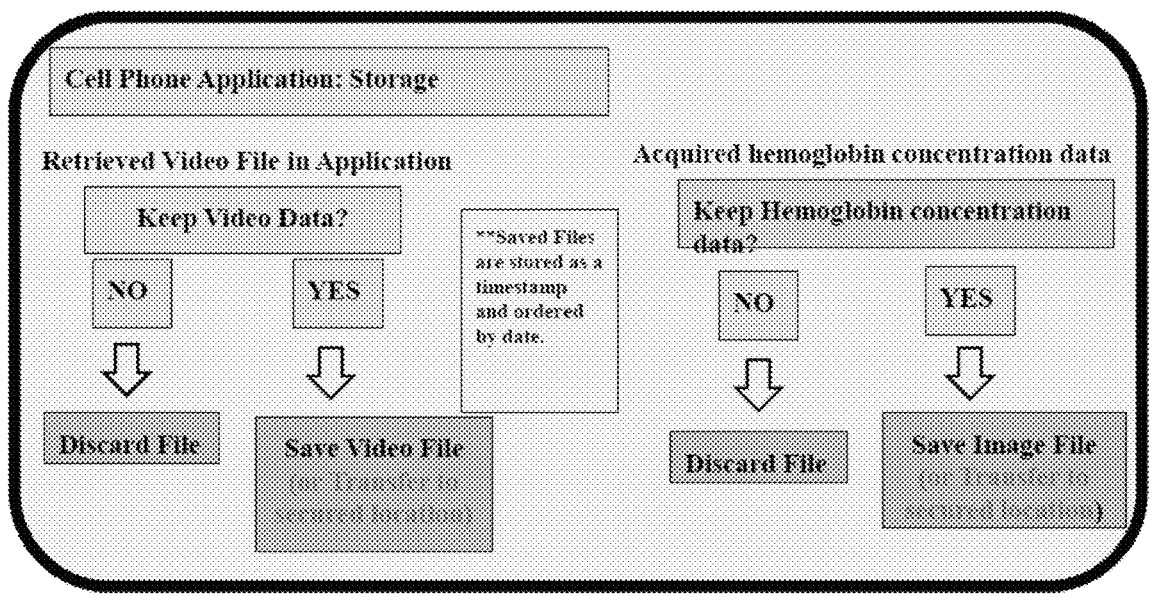
FIG. 16(a) shows instructions for storing raw and final data in an application of a cellphone-based oxygenation tool according to an embodiment of the subject invention.
Figure 16B:
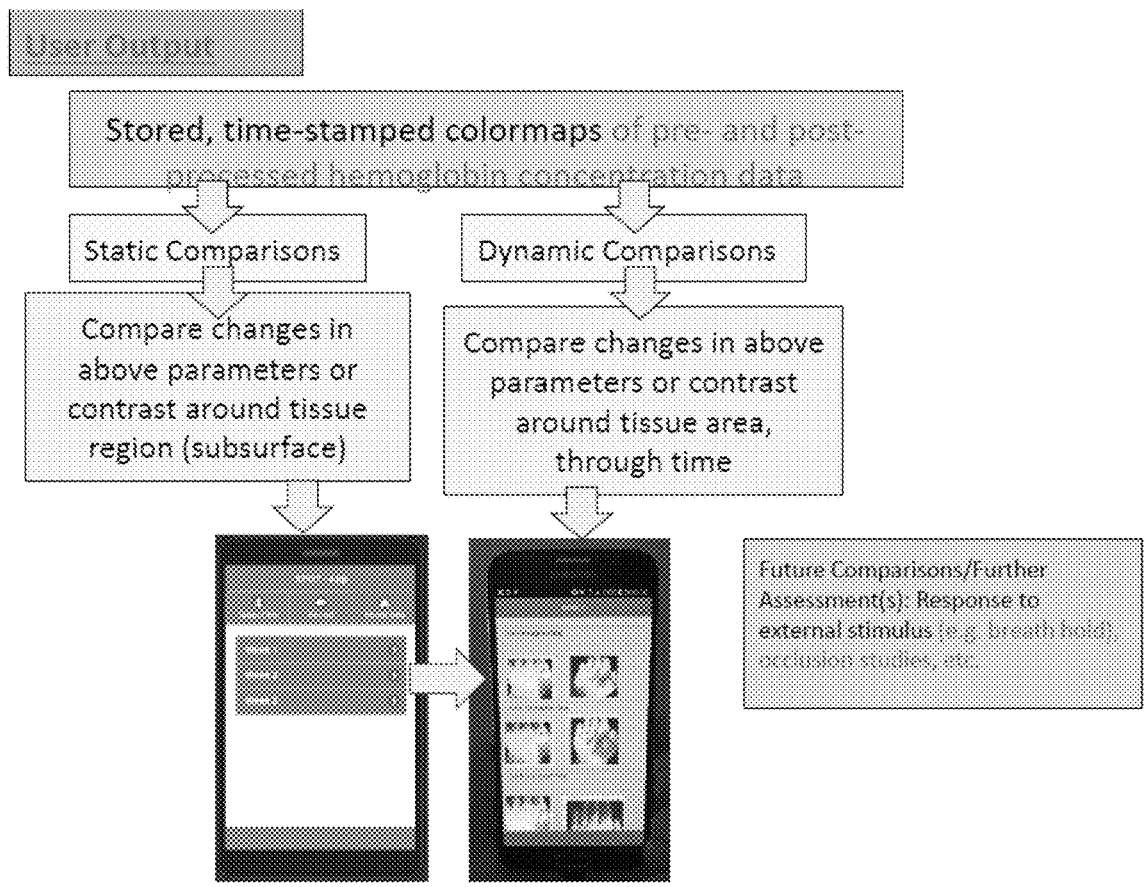
FIG. 16(b) shows a user output of a cellphone-based oxygenation tool according to an embodiment of the subject invention.

The device collects data across all wavelengths of interest by multiplexing across the chosen wavelengths. If the data is collected appropriately, recorded video will be saved when prompted by the application. FIG. 16(a) shows instructions for storing (can also be uploaded to a remote server (e.g., cloud or FTP server) via for example Bluetooth, USB, or Wi-Fi) raw and final data in an application of a cellphone-based oxygenation tool according to an embodiment of the subject invention, and FIG. 16(b) shows a user output of a cellphone-based oxygenation tool according to an embodiment of the subject invention. The output from initial processing results in 3 images (or 6 if including calibration images) at 3 (or 1 or 2 or 4 or more) different wavelengths that undergo hemodynamic analysis. During the hemodynamic analysis at the processing stage, pixel intensity data is converted into oxygenated and deoxygenated hemoglobin concentrations (using appropriate Modified Beer-Lambert's law or other light propagation models and appropriate numerical techniques to optimize via iterative methods, regression analysis, or appropriate reconstruction algorithms). Hemoglobin concentration maps (e.g., a pseudo-color map of reconstructed parameters) are shown across a tissue region in terms of intensity with red corresponding to 100% change in HbO and blue representing 0% change in HbO. Maps can also be in terms of changes in HbR, HbT, oxygen saturation ($StO_2$=HbO/HbT), a combination of one or more of these tissue oxygenation parameters, their contrasts, and/or their derivatives. Data will be stored only if the user agrees when prompted by the application at the end of final processing. Images are stored as their date and time for easy comparison of images through time.

Embodiments of the subject invention include low-cost CBOTs that have an add-on imaging tool along with an integrated smartphone-app to allow automated data acquisition, analysis and storage.

Multiple LEDs can be used to increase field of illumination (FOI). The CBOT according to an embodiment of the subject invention can incorporate Bluetooth and/or z wave technology (wireless radio frequency-based communications) that can deliver high quality networking while operating at low energy (compared to Wi-Fi), to allow for hardware control from smart phone app.

The App of the CBOT is developed for design of a custom, user-friendly app on a cloud based platform providing user interface (UI) development tools and backend services built with appropriate software (e.g., jQuery Mobile/Bootstrap/Ionic, JavaScript) for the purpose of storing de-identified subject information, data recording/saving/retrieval, and data analysis/processing to acquire absorption contrast. The data can also be retrieved from the cellphone via for example Bluetooth, Wi-Fi, or via USB from a remote server (e.g., cloud or FTP server). The information can be initially stored within the device's internal memory, but can then be uploaded to a remote server, or retrieved on an external memory source, if the cellphone offers this capability.

The CBOT device can be controlled using Bluetooth and/or z-wave technology by an external trigger in a source-routed mesh network topology connecting devices (one or more) to the smartphone, while the native device features or internal hardware (such as the digital camera) will be controlled and synced by the custom-app resulting in a 3-part device (add on imaging tool+smartphone+app CBOT). Hardware modifications can be made to multiplex wavelengths and synchronize illumination and detection by smartphone (using Bluetooth and/or z wave technology). Image stabilizing tools can be used to reduce noise and movement during imaging. The software app can be modified to process hemodynamic analysis using modified Beer Lambert's law or other light propagation models that mimic transport of diffused light.

Figures 17A, 17B, 17C:
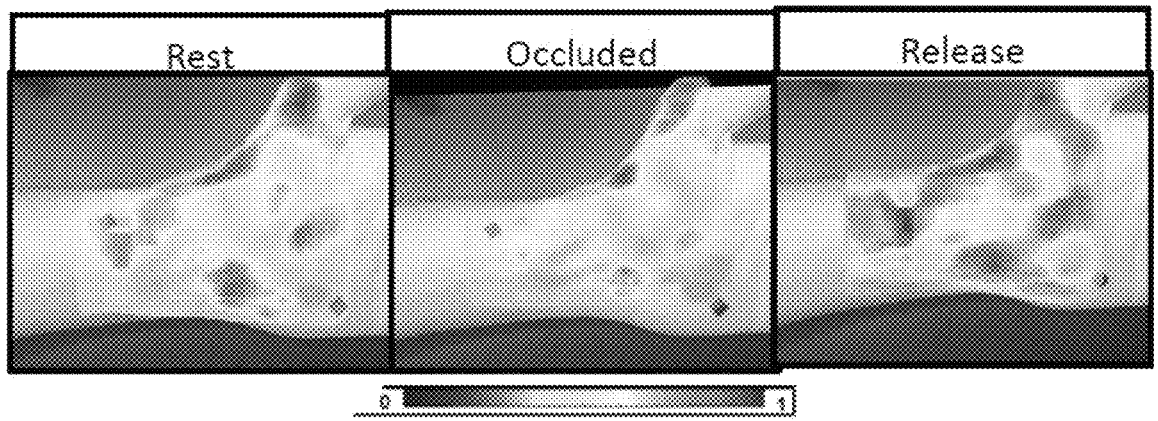
FIGS. 17(a)-(c) show diffuse reflectance images due to occlusion, after applying singular value decomposition (SVD) image reconstruction for noise removal. Reconstructed diffuse reflectance images are shown across three time stamps (rest—FIG. 17(a), occluded—FIG. 17(b), and release—FIG. 17(c)) in a control subject, in response to occlusion. An SVD-based approach was used to reconstruct the images, thereby removing surface noise. The reconstruction was performed using Eigen values of 4:15.

NIR imaging studies were performed using the CBOT in response to venous occlusion studies. Occlusion causes changes in blood flow, which relates to physiological changes of the tissue region occluded. Because NIR-based optical imaging techniques can determine physiological changes, occlusions studies are widely used as a validation study. Singular value decomposition (SVD) is a widely used image processing technique that is implemented to medical imaging data to reduce the image dimensionality. It extracts relevant details by reducing the dimensionality of the data via a simple implementation. SVD has been used extensively in the past for image compression and noise removal. SVD was implemented to the diffuse reflectance data at each wavelength. Reconstructed images of diffuse reflectance at a given wavelength (here only 690 nm data was used during preliminary assessment of the device) were compared across the three time stamps (rest, occlusion, and release) and SVD was applied for noise removal. The optical images varied across the time stamps (i.e., rest, occlusion, and relax) when Eigen values (EVs) between 3:15, 4:15, and/or 5:15 were used and further removal of EVs diminished that difference. FIGS. 17(a)-(c) show the diffuse reflectance images across the time stamps for four subjects for results obtained when using 4:15 EV-based SVD analysis. The differences in the diffuse reflectance images (or optical images) across the three time stamps appear distinct demonstrating that occlusion changes can be captured by CBOT.

Figures 18A, 18B, 18C:
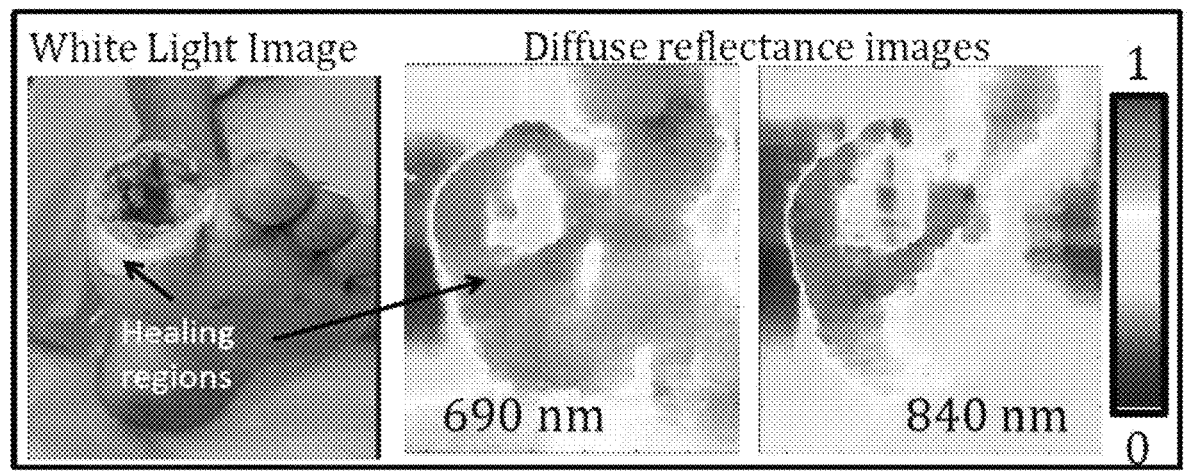
FIG. 18(a) shows post-operative healing diabetic foot ulcer (DFU).
FIG. 18(b) shows a diffuse reflectance image using a cellphone-based oxygenation tool (CBOT) with 690 nm light source according to an embodiment of the subject invention.
FIG. 18(c) shows a diffuse reflectance image using a cellphone-based oxygenation tool (CBOT) with 840 nm light source according to an embodiment of the subject invention.

FIG. 18(a) shows post-operative healing diabetic foot ulcer (DFU), FIG. 18(b) shows a diffuse reflectance image using a cellphone-based oxygenation tool (CBOT) with 690 nm light source according to an embodiment of the subject invention, and FIG. 18(c) shows a diffuse reflectance image using a cellphone-based oxygenation tool (CBOT) with 840 nm light source according to an embodiment of the subject invention. Referring to FIGS. 18(a)-18(c), diffuse reflectance images are shown at two discrete NIR wavelengths (690 nm and 840 nm) from a healing DFU (in-patient). There is a distinct contrast in diffuse reflectance in the ulcer's center (not healed) to the healing peripheries (as observed from epithelization or pink color in FIG. 18(a)). These results help differentiate healing from non-healing regions in DFUs and correlate to other diffuse reflectance images obtained using an NIR optical scanner on DFUs.

The methods and processes described herein can be embodied as code and/or data. The software code and data described herein can be stored on one or more machine-readable media (e.g., computer-readable media), which may include any device or medium that can store code and/or data for use by a computer system. When a computer system and/or processer reads and executes the code and/or data stored on a computer-readable medium, the computer system and/or processer performs the methods and processes embodied as data structures and code stored within the computer-readable storage medium.

It should be appreciated by those skilled in the art that computer-readable media include removable and non-removable structures/devices that can be used for storage of information, such as computer-readable instructions, data structures, program modules, and other data used by a computing system/environment. A computer-readable medium includes, but is not limited to, volatile memory such as random access memories (RAM, DRAM, SRAM); and non-volatile memory such as flash memory, various read-only-memories (ROM, PROM, EPROM, EEPROM), magnetic and ferromagnetic/ferroelectric memories (MRAM, FeRAM), and magnetic and optical storage devices (hard drives, magnetic tape, CDs, DVDs); network devices; or other media now known or later developed that are capable of storing computer-readable information/data. Computer-readable media should not be construed or interpreted to include any propagating signals. A computer-readable medium of embodiments of the subject invention can be, for example, a compact disc (CD), digital video disc (DVD), flash memory device, volatile memory, or a hard disk drive (HDD), such as an external HDD or the HDD of a computing device, though embodiments are not limited thereto. A computing device can be, for example, a laptop computer, desktop computer, server, cell phone, or tablet, though embodiments are not limited thereto.

It should be understood that the examples and embodiments described herein are for illustrative purposes only and that various modifications or changes in view thereof will be suggested to persons skilled in the art and are to be included within the spirit and purview of this application.

All patents, patent applications, provisional applications, and publications referred to or cited herein are incorporated by reference in their entirety, including all figures and tables, to the extent they are not inconsistent with the explicit teachings of this specification.

What is claimed is:

1. A cellphone-based tool for measuring tissue oxygenation of a sample, the cellphone-based tool comprising:
   a circuitry housing;
   a light source case disposed on the circuitry housing;
   a lens holder disposed on the circuitry housing; and
   a light source disposed in the light source case and configured for emitting light on the sample;
   a near-infrared (NIR) filter disposed on the circuit housing;
   a cellphone disposed on the circuitry housing, the cellphone comprising a camera that is NIR sensitive,
   the cellphone configured for receiving an image of the sample through the NIR filter, processing a pixel intensity of the image, and converting the pixel intensity into a plurality of hemoglobin concentration maps comprising a first hemoglobin concentration map based on oxygenated hemoglobin concentration, a second hemoglobin concentration map based on deoxygenated hemoglobin concentration, a third hemoglobin concentration map based on total hemoglobin concentration, and a fourth hemoglobin concentration map based on oxygen saturation,
   the cellphone further configured for generating a tissue oxygenation map of the sample based on the plurality of hemoglobin concentration maps.

2. The cellphone-based tool according to claim 1, further comprising at least one of a diffuser sheet, a diffuser lens, a polarizer lens, and a polarizer sheet on the light source case.

3. The cellphone-based tool according to claim 2, the NIR filter comprising at least one of a longpass filter, a bandpass filter, a holographic filter, a polarizer lens, and a polarizer sheet.

4. The cellphone-based tool according to claim 2, the light source comprising a plurality of light emitting diodes (LEDs), each LED of the plurality of LEDs being a multi-wavelength LED capable of emitting light at multiple wavelengths.

5. The cellphone-based tool according to claim 4, the circuitry housing comprising a first housing having the cellphone disposed thereon and a second housing including the light source case.

6. The cellphone-based tool according to claim 5, further comprising an adjustable mount disposed between the first housing and the second housing.

7. The cellphone-based tool according to claim 6, the adjustable mount comprising a horizontal adjuster and a vertical adjuster.

8. The cellphone-based tool according to claim 6, further comprising a handle disposed on the first housing.

9. The cellphone-based tool according to claim 1, the cellphone-based tool configured for performing fluorescence imaging.

10. A method of measuring tissue oxygenation of a sample using a cellphone-based tool, the method comprising:
   providing a circuitry housing comprising a light source case, a lens holder, and a near-infrared (NIR) filter disposed thereon, the light source case comprising a light source disposed therein;
   connecting a cellphone to the circuitry housing, the cellphone comprising a camera that is NIR sensitive, the cellphone being connected to the circuitry housing such that the camera of the cellphone is aligned with the NIR filter;
   emitting, by the light source, light on the sample;
   receiving, by the cellphone, an image through the NIR filter;
   processing, by the cellphone, a pixel intensity based on the image;
   converting, by the cellphone, the pixel intensity into a plurality of hemoglobin concentration maps comprising a first hemoglobin concentration map based on oxygenated hemoglobin concentration, a second hemoglobin concentration map based on deoxygenated hemoglobin concentration, a third hemoglobin concentration map based on total hemoglobin concentration, and a fourth hemoglobin concentration map based on oxygen saturation;
   generating, by the cellphone, a tissue oxygenation map of the sample based on the plurality of hemoglobin concentration maps; and
   storing the tissue oxygenation map and the plurality of hemoglobin concentration maps on the cellphone.

11. The method according to claim 10, the emitting light by the light source comprising selecting a single wavelength mode or a multiple wavelength mode.

12. The method according to claim 11, the emitting light by the light source comprising outputting light at multiple wavelengths with or without multiplexing under the multiple wavelength mode.

13. The method according to claim 11, the emitting light by the light source comprising outputting a single wavelength continuously.

14. The method according to claim 10, further comprising positioning a calibration paper.

15. The method according to claim 14, the image comprising a video file,
   the video file being separated into calibration frames and data frames of each multiplexed wavelength of a plurality of multiplexed wavelengths, and
   the positioning of the calibration paper comprising positioning the calibration paper such that it aligns with the calibration frames.

16. The method according to claim 10, the image comprising at least one of a video file and an image file.

17. The method according to claim 11, further comprising comparing parameters or contrast of the stored tissue oxygenation map or plurality of hemoglobin concentration maps.

18. A cellphone-based tool for measuring tissue oxygenation of a sample, the cellphone-based tool comprising:
   a circuitry housing;
   a light emitting diode (LED) box disposed on the circuitry housing;
   a plurality of LEDs disposed in the LED box and configured for emitting light on the sample;
   a diffuser sheet or diffuser lens disposed on the LED box;
   a lens holder disposed on the circuitry housing and configured to be movable with respect to the circuitry housing;
   a near-infrared (NIR) filter disposed on the circuit housing; and
   a cellphone disposed on the circuitry housing, the cellphone comprising a camera that is NIR sensitive,
   the cellphone configured for receiving an image of the sample through the NIR filter, processing a pixel intensity of the image, and converting the pixel intensity into a plurality of hemoglobin concentration maps comprising a first hemoglobin concentration map based on oxygenated hemoglobin concentration, a second hemoglobin concentration map based on deoxygenated hemoglobin concentration, a third hemoglobin concentration map based on total hemoglobin concentration, and a fourth hemoglobin concentration map based on oxygen saturation,
   the cellphone further configured for generating a tissue oxygenation map of the sample based on the plurality of hemoglobin concentration maps,
   the circuitry housing comprising a first housing having the cellphone disposed thereon and a second housing connected to the first housing,
   the cellphone-based tool further comprising: a handle disposed on the first housing; and an adjustable mount disposed between the first housing and the second housing, the adjustable mount comprising a horizontal adjuster and a vertical adjuster, and
   each LED of the plurality of LEDs being a multi-wavelength LED capable of emitting light at multiple wavelengths.

* * * * *